US009840725B2

(12) United States Patent
Gusyatiner et al.

(10) Patent No.: US 9,840,725 B2
(45) Date of Patent: Dec. 12, 2017

(54) **METHOD FOR PRODUCING AN L-AMINO ACID USING A BACTERIUM OF THE FAMILY *ENTEROBACTERIACEAE* HAVING A DISRUPTED PUTRESCINE DEGRADATION PATHWAY**

(71) Applicant: AJINOMOTO CO., INC., Tokyo (JP)

(72) Inventors: Mikhail Markovich Gusyatiner, Moscow (RU); Yulia Georgievna Rostova, Moscow (RU); Mikhail Yurievich Kiryukhin, Moscow (RU); Anastasia Yurienva Romkina, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/097,500

(22) Filed: Apr. 13, 2016

(65) Prior Publication Data
US 2016/0237464 A1 Aug. 18, 2016

Related U.S. Application Data

(63) Continuation of application No. PCT/JP2014/078157, filed on Oct. 16, 2014.

(30) Foreign Application Priority Data

Oct. 28, 2013 (RU) .................................. 2013147882

(51) Int. Cl.
  C12P 13/10 (2006.01)
  C12P 13/24 (2006.01)
  C12P 13/14 (2006.01)

(52) U.S. Cl.
  CPC ............... *C12P 13/24* (2013.01); *C12P 13/10* (2013.01); *C12P 13/14* (2013.01)

(58) Field of Classification Search
  CPC ............ C12P 13/10; C12P 13/14; C12P 13/24
  See application file for complete search history.

(56) References Cited

U.S. PATENT DOCUMENTS

| | | | |
|---|---|---|---|
| 4,278,765 A | 7/1981 | Debabov et al. |
| 4,346,170 A | 8/1982 | Sano et al. |
| 5,661,012 A | 8/1997 | Sano et al. |
| 5,965,391 A | 10/1999 | Reinscheid et al. |
| 5,998,178 A | 12/1999 | Hashiguchi et al. |
| 6,040,160 A | 3/2000 | Kojima et al. |
| 8,227,214 B2 | 7/2012 | Rybak et al. |
| 8,647,838 B2 | 2/2014 | Kiryukhin et al. |
| 8,691,537 B2 | 4/2014 | Filippov et al. |
| 8,703,446 B2 | 4/2014 | Kiryukhin et al. |
| 8,722,370 B2 | 5/2014 | Filippov et al. |
| 8,728,774 B2 | 5/2014 | Rybak et al. |
| 8,785,161 B2 | 7/2014 | Rybak et al. |
| 9,029,104 B2 | 5/2015 | Samsonova et al. |
| 2006/0216796 A1 | 9/2006 | Hashiguchi et al. |
| 2010/0203599 A1 | 8/2010 | Lee et al. |
| 2012/0237986 A1 | 9/2012 | Ziyatdinov et al. |
| 2013/0078681 A1 | 3/2013 | Rostova et al. |
| 2014/0287472 A1 | 9/2014 | Rybak et al. |

FOREIGN PATENT DOCUMENTS

| | | |
|---|---|---|
| EP | 0685555 A1 | 12/1995 |
| EP | 2281880 A2 | 2/2011 |
| JP | 2013-176301 A | 9/2013 |
| WO | WO95/16042 A1 | 6/1995 |
| WO | WO96/15246 A1 | 5/1996 |
| WO | WO02/097086 A1 | 12/2002 |
| WO | WO2011/152568 A1 | 12/2011 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Sadowski et al., Current Opinion in Structural Biology 19:357-362, 2009.*
Kurihara et al., Journal of Biological Chemistry 283(29):19981-19992, 2008.*
Schneider et al. Journal of Bacteriology 184(24):6976-6986, 2002.*
Sousa et al., Microbiology 148(Pt5):1291-1303, 2002.*
Branch, A., TIBS 23:45-50, 1998.*
Schneider, B. L., et al., "Putrescine catabolism is a metabolic response to several stresses in *Escherichia coli*," Mol. Microbiol. 2013;88(3):537-550.
Bandounas, L., et al., "Redundancy in putrescine catabolism in solvent tolerant Pseudomonas putida S12," J. Biotechnol. 2011;154:1-10.
Niemoto, N., et al., "Mechanism for Regulation of the Putrescine Utilization Pathway by the Transcription Factor PuuR in *Escherichia coli* K-12," J. Bacteriol. 2012;194(13):3437-3447.
International Search Report for PCT Patent App. No. PCT/JP2014/078157 (dated Feb. 5, 2015).
Written Opinion for PCT Patent App. No. PCT/JP2014/078157 (dated Feb. 5, 2015).
Schneider, B. L., et al., "Arginine Catabolism and the Arginine Succinyltransferase Pathway in *Escherichia coli*," J. Bacteriol. 1998;180(16):4278-4286.
Office Action from Japanese Patent App. No. 2016-542494 dated Jan. 31, 2017 with English language translation thereof.

(Continued)

*Primary Examiner* — Delia Ramirez
(74) *Attorney, Agent, or Firm* — Shelly Guest Cermak; Cermak Nakajima & McGowan LLP

(57) ABSTRACT

The present invention provides a method for producing L-amino acids such as L-amino acids belonging to the glutamate family by fermentation using a bacterium of the family Enterobacteriaceae, particularly a bacterium belonging to the genus *Escherichia*, which has been modified to disrupt the putrescine degradation pathway by, for example, inactivation of one gene or several genes from the puuADRCBE gene cluster.

6 Claims, No Drawings

(56) References Cited

OTHER PUBLICATIONS

Kurihara, S., et al., "A Novel Putrescine Utilization Pathway Involves y-Glutamylated Intermediates of *Escherichia coli* K-12," J. Biol. Chem. 2005;280(6)4602-4608.

Qian, Z.-G., et al., "Metabolic Engineering of *Escherichia coli* for the Production of Putrescine: A Four Carbon Diamine," Biotechnol. Bioeng. 2009;104(4):651-662.

Office Action from Japanese Patent App. No. 2016-542494 (dated Apr. 11, 2017) with English language machine translation.

* cited by examiner

SEQUENCE LISTING

<160> NUMBER OF SEQ ID NOS: 20

<210> SEQ ID NO 1
<211> LENGTH: 1419
<212> TYPE: DNA
<213> ORGANISM: Escherichia coli
<220> FEATURE:
<221> NAME/KEY: CDS
<222> LOCATION: (1)..(1419)

<400> SEQUENCE: 1

| | | | | | | | | | | | | | | | | |
|---|---|---|---|---|---|---|---|---|---|---|---|---|---|---|---|---|
| atg | gaa | acc | aat | atc | gtt | gaa | gta | gag | aac | ttt | gtt | cag | cag | tca | gaa | 48 |
| Met | Glu | Thr | Asn | Ile | Val | Glu | Val | Glu | Asn | Phe | Val | Gln | Gln | Ser | Glu | |
| 1 | | | | 5 | | | | | 10 | | | | | 15 | | |
| gag | agg | cgg | ggt | agc | gcc | ttt | acg | cag | gaa | gtg | aaa | cgc | tac | ctg | gag | 96 |
| Glu | Arg | Arg | Gly | Ser | Ala | Phe | Thr | Gln | Glu | Val | Lys | Arg | Tyr | Leu | Glu | |
| | | | 20 | | | | | 25 | | | | | 30 | | | |
| cgc | tac | ccg | aat | acg | caa | tat | gtt | gat | gtt | tta | ctt | acc | gat | tta | aat | 144 |
| Arg | Tyr | Pro | Asn | Thr | Gln | Tyr | Val | Asp | Val | Leu | Leu | Thr | Asp | Leu | Asn | |
| | | 35 | | | | | 40 | | | | | 45 | | | | |
| ggt | tgc | ttc | cgt | gga | aag | cgt | att | cct | gtt | tca | agc | ctg | aag | aag | ctc | 192 |
| Gly | Cys | Phe | Arg | Gly | Lys | Arg | Ile | Pro | Val | Ser | Ser | Leu | Lys | Lys | Leu | |
| | 50 | | | | | 55 | | | | | 60 | | | | | |
| gag | aaa | ggg | tgt | tat | ttc | ccg | gcc | tcg | gta | ttt | gca | atg | gat | att | ctg | 240 |
| Glu | Lys | Gly | Cys | Tyr | Phe | Pro | Ala | Ser | Val | Phe | Ala | Met | Asp | Ile | Leu | |
| 65 | | | | | 70 | | | | | 75 | | | | | 80 | |
| ggc | aac | gta | gta | gaa | gaa | gca | ggt | ctg | ggt | cag | gaa | atg | ggc | gag | ccg | 288 |
| Gly | Asn | Val | Val | Glu | Glu | Ala | Gly | Leu | Gly | Gln | Glu | Met | Gly | Glu | Pro | |
| | | | | 85 | | | | | 90 | | | | | 95 | | |
| gat | cgt | acc | tgt | gtt | cct | gtt | ctc | ggt | tcc | tta | act | cct | tct | gcc | gcc | 336 |
| Asp | Arg | Thr | Cys | Val | Pro | Val | Leu | Gly | Ser | Leu | Thr | Pro | Ser | Ala | Ala | |
| | | | 100 | | | | | 105 | | | | | 110 | | | |
| gat | cca | gag | ttt | atc | ggt | cag | atg | ctc | ctg | acc | atg | gtc | gat | gaa | gat | 384 |
| Asp | Pro | Glu | Phe | Ile | Gly | Gln | Met | Leu | Leu | Thr | Met | Val | Asp | Glu | Asp | |
| | | 115 | | | | | 120 | | | | | 125 | | | | |
| ggc | gct | ccc | ttt | gac | gtt | gag | ccg | cgg | aac | gtt | ctt | aac | cgc | ctg | tgg | 432 |
| Gly | Ala | Pro | Phe | Asp | Val | Glu | Pro | Arg | Asn | Val | Leu | Asn | Arg | Leu | Trp | |
| | 130 | | | | | 135 | | | | | 140 | | | | | |
| cag | cag | ctg | cgc | cag | cgc | gga | ttg | ttc | ccg | gtc | gta | gcg | gta | gag | ctg | 480 |
| Gln | Gln | Leu | Arg | Gln | Arg | Gly | Leu | Phe | Pro | Val | Val | Ala | Val | Glu | Leu | |
| 145 | | | | | 150 | | | | | 155 | | | | | 160 | |
| gag | ttc | tat | tta | ctg | gat | cgc | cag | cgc | gac | gct | gaa | ggg | tat | ctg | caa | 528 |
| Glu | Phe | Tyr | Leu | Leu | Asp | Arg | Gln | Arg | Asp | Ala | Glu | Gly | Tyr | Leu | Gln | |
| | | | | 165 | | | | | 170 | | | | | 175 | | |
| ccg | ccc | tgc | gcg | cct | ggc | acc | gat | gac | cgc | aat | aca | caa | agc | cag | gtt | 576 |
| Pro | Pro | Cys | Ala | Pro | Gly | Thr | Asp | Asp | Arg | Asn | Thr | Gln | Ser | Gln | Val | |
| | | | 180 | | | | | 185 | | | | | 190 | | | |
| tac | tcc | gtt | gat | aac | ctc | aac | cac | ttc | gcc | gac | gtg | ctc | aat | gat | att | 624 |
| Tyr | Ser | Val | Asp | Asn | Leu | Asn | His | Phe | Ala | Asp | Val | Leu | Asn | Asp | Ile | |
| | | 195 | | | | | 200 | | | | | 205 | | | | |
| gat | gaa | ctg | gcg | cag | tta | cag | ctg | att | ccg | gca | gat | ggc | gcg | gtc | gct | 672 |
| Asp | Glu | Leu | Ala | Gln | Leu | Gln | Leu | Ile | Pro | Ala | Asp | Gly | Ala | Val | Ala | |
| | 210 | | | | | 215 | | | | | 220 | | | | | |
| gag | gcc | tcg | ccg | ggt | cag | ttt | gaa | atc | aac | ctt | tac | cat | act | gat | aac | 720 |
| Glu | Ala | Ser | Pro | Gly | Gln | Phe | Glu | Ile | Asn | Leu | Tyr | His | Thr | Asp | Asn | |
| 225 | | | | | 230 | | | | | 235 | | | | | 240 | |
| gtg | ctg | gaa | gcc | tgc | gat | gat | gcg | ctg | gca | cta | aaa | cgc | ctg | gtg | cgt | 768 |
| Val | Leu | Glu | Ala | Cys | Asp | Asp | Ala | Leu | Ala | Leu | Lys | Arg | Leu | Val | Arg | |
| | | | | 245 | | | | | 250 | | | | | 255 | | |
| ctg | atg | gca | gaa | aag | cat | aag | atg | cac | gcc | act | ttt | atg | gcg | aag | ccg | 816 |
| Leu | Met | Ala | Glu | Lys | His | Lys | Met | His | Ala | Thr | Phe | Met | Ala | Lys | Pro | |

```
                 260                 265                 270
tat gaa gag cac gcg ggc agc gga atg cat atc cat atc agt atg caa         864
Tyr Glu Glu His Ala Gly Ser Gly Met His Ile His Ile Ser Met Gln
                 275                 280                 285 aat aat cgt ggc gag aac gtg ctt tct gac gcg gaa ggc gaa gat tcg         912
Asn Asn Arg Gly Glu Asn Val Leu Ser Asp Ala Glu Gly Glu Asp Ser
                 290                 295                 300 ccg ctg ctg aaa aag atg ctc gcc ggg atg att gac ctg atg ccg tcg         960
Pro Leu Leu Lys Lys Met Leu Ala Gly Met Ile Asp Leu Met Pro Ser
305                 310                 315                 320 tcg atg gcg ttg ctg gca cca aac gtg aac tcg tat cgc cgc ttc cag        1008
Ser Met Ala Leu Leu Ala Pro Asn Val Asn Ser Tyr Arg Arg Phe Gln
                 325                 330                 335 ccg gga atg tat gtg ccg acg cag gcg tcg tgg ggc cat aac aac cgc        1056
Pro Gly Met Tyr Val Pro Thr Gln Ala Ser Trp Gly His Asn Asn Arg
                 340                 345                 350 acc gtc gcc ctg cgt att ccg tgc ggc gac cgt cat aat cac cgc gtg        1104
Thr Val Ala Leu Arg Ile Pro Cys Gly Asp Arg His Asn His Arg Val
                 355                 360                 365 gaa tat cgc gtg gcg ggt gcc gat gcc aac cca tat ctg gtg atg gca        1152
Glu Tyr Arg Val Ala Gly Ala Asp Ala Asn Pro Tyr Leu Val Met Ala
                 370                 375                 380 gcg att ttt gcc ggt att ttg cat ggc ctt gat aac gag ctg ccg ttg        1200
Ala Ile Phe Ala Gly Ile Leu His Gly Leu Asp Asn Glu Leu Pro Leu
385                 390                 395                 400 cag gaa gaa gtc gaa ggc aac ggg ctg gaa cag gaa ggc tta ccc ttt        1248
Gln Glu Glu Val Glu Gly Asn Gly Leu Glu Gln Glu Gly Leu Pro Phe
                 405                 410                 415 ccg att cgc cag agc gat gcc ctg ggt gag ttt atc gag aat gat cac        1296
Pro Ile Arg Gln Ser Asp Ala Leu Gly Glu Phe Ile Glu Asn Asp His
                 420                 425                 430 ctg cgc cgc tat tta ggc gaa cgc ttc tgc cat gtc tat cac gcc tgt        1344
Leu Arg Arg Tyr Leu Gly Glu Arg Phe Cys His Val Tyr His Ala Cys
                 435                 440                 445 aaa aat gat gag ctg ttg cag ttt gag cgc ctc atc aca gaa aca gaa        1392
Lys Asn Asp Glu Leu Leu Gln Phe Glu Arg Leu Ile Thr Glu Thr Glu
                 450                 455                 460 att gag tgg atg ttg aaa aac gcg taa                                    1419
Ile Glu Trp Met Leu Lys Asn Ala
465                 470

<210> SEQ ID NO 2
<211> LENGTH: 472
<212> TYPE: PRT
<213> ORGANISM: Escherichia coli

<400> SEQUENCE: 2

Met Glu Thr Asn Ile Val Glu Val Glu Asn Phe Val Gln Gln Ser Glu
1               5                   10                  15

Glu Arg Arg Gly Ser Ala Phe Thr Gln Glu Val Lys Arg Tyr Leu Glu
                20                  25                  30

Arg Tyr Pro Asn Thr Gln Tyr Val Asp Val Leu Leu Thr Asp Leu Asn
            35                  40                  45

Gly Cys Phe Arg Gly Lys Arg Ile Pro Val Ser Ser Leu Lys Lys Leu
        50                  55                  60

Glu Lys Gly Cys Tyr Phe Pro Ala Ser Val Phe Ala Met Asp Ile Leu
65                  70                  75                  80

Gly Asn Val Val Glu Glu Ala Gly Leu Gly Gln Glu Met Gly Glu Pro
                85                  90                  95
```

Asp Arg Thr Cys Val Pro Val Leu Gly Ser Leu Thr Pro Ser Ala Ala
            100                 105                 110

Asp Pro Glu Phe Ile Gly Gln Met Leu Leu Thr Met Val Asp Glu Asp
            115                 120                 125

Gly Ala Pro Phe Asp Val Glu Pro Arg Asn Val Leu Asn Arg Leu Trp
130                 135                 140

Gln Gln Leu Arg Gln Arg Gly Leu Phe Pro Val Val Ala Val Glu Leu
145                 150                 155                 160

Glu Phe Tyr Leu Leu Asp Arg Gln Arg Asp Ala Glu Gly Tyr Leu Gln
                165                 170                 175

Pro Pro Cys Ala Pro Gly Thr Asp Asp Arg Asn Thr Gln Ser Gln Val
            180                 185                 190

Tyr Ser Val Asp Asn Leu Asn His Phe Ala Asp Val Leu Asn Asp Ile
            195                 200                 205

Asp Glu Leu Ala Gln Leu Gln Leu Ile Pro Ala Asp Gly Ala Val Ala
            210                 215                 220

Glu Ala Ser Pro Gly Gln Phe Glu Ile Asn Leu Tyr His Thr Asp Asn
225                 230                 235                 240

Val Leu Glu Ala Cys Asp Asp Ala Leu Ala Leu Lys Arg Leu Val Arg
                245                 250                 255

Leu Met Ala Glu Lys His Lys Met His Ala Thr Phe Met Ala Lys Pro
                260                 265                 270

Tyr Glu Glu His Ala Gly Ser Gly Met His Ile His Ile Ser Met Gln
            275                 280                 285

Asn Asn Arg Gly Glu Asn Val Leu Ser Asp Ala Glu Gly Glu Asp Ser
            290                 295                 300

Pro Leu Leu Lys Lys Met Leu Ala Gly Met Ile Asp Leu Met Pro Ser
305                 310                 315                 320

Ser Met Ala Leu Leu Ala Pro Asn Val Asn Ser Tyr Arg Arg Phe Gln
                325                 330                 335

Pro Gly Met Tyr Val Pro Thr Gln Ala Ser Trp Gly His Asn Asn Arg
            340                 345                 350

Thr Val Ala Leu Arg Ile Pro Cys Gly Asp Arg His Asn His Arg Val
            355                 360                 365

Glu Tyr Arg Val Ala Gly Ala Asp Ala Asn Pro Tyr Leu Val Met Ala
370                 375                 380

Ala Ile Phe Ala Gly Ile Leu His Gly Leu Asp Asn Glu Leu Pro Leu
385                 390                 395                 400

Gln Glu Glu Val Glu Gly Asn Gly Leu Glu Gln Glu Gly Leu Pro Phe
                405                 410                 415

Pro Ile Arg Gln Ser Asp Ala Leu Gly Glu Phe Ile Glu Asn Asp His
            420                 425                 430

Leu Arg Arg Tyr Leu Gly Glu Arg Phe Cys His Val Tyr His Ala Cys
            435                 440                 445

Lys Asn Asp Glu Leu Leu Gln Phe Glu Arg Leu Ile Thr Glu Thr Glu
            450                 455                 460

Ile Glu Trp Met Leu Lys Asn Ala
465                 470

<210> SEQ ID NO 3
<211> LENGTH: 765
<212> TYPE: DNA
<213> ORGANISM: Escherichia coli
<220> FEATURE:

-continued

<221> NAME/KEY: CDS
<222> LOCATION: (1)..(765)

<400> SEQUENCE: 3

```
atg gaa aat ata atg aac aat ccg gtt atc ggt gtc gta atg tgc agg      48
Met Glu Asn Ile Met Asn Asn Pro Val Ile Gly Val Val Met Cys Arg
1               5                   10                  15 aac agg ctt aag ggt cat gcg acc cag act ctg caa gaa aag tac ctg      96
Asn Arg Leu Lys Gly His Ala Thr Gln Thr Leu Gln Glu Lys Tyr Leu
            20                  25                  30 aat gcc atc atc cat gca ggc ggc ttg cct att gcg cta cca cat gcg     144
Asn Ala Ile Ile His Ala Gly Gly Leu Pro Ile Ala Leu Pro His Ala
        35                  40                  45 ctg gcg gaa ccg tca tta ctt gaa caa ctt ttg ccg aaa ctc gat ggc     192
Leu Ala Glu Pro Ser Leu Leu Glu Gln Leu Leu Pro Lys Leu Asp Gly
    50                  55                  60 att tat ctt cct ggt agt ccc agc aat gtg cag ccg cac cta tat ggt     240
Ile Tyr Leu Pro Gly Ser Pro Ser Asn Val Gln Pro His Leu Tyr Gly
65                  70                  75                  80 gaa aac ggc gat gag cct gac gcc gat ccc ggg cgt gat ctt ctg agc     288
Glu Asn Gly Asp Glu Pro Asp Ala Asp Pro Gly Arg Asp Leu Leu Ser
                85                  90                  95 atg gcg ata att aat gcc gca ctc gaa agg cgc atc ccc att ttc gcc     336
Met Ala Ile Ile Asn Ala Ala Leu Glu Arg Arg Ile Pro Ile Phe Ala
            100                 105                 110 atc tgc cgg ggt tta caa gaa ctg gtg gtg gca acc ggt ggt tcg ttg     384
Ile Cys Arg Gly Leu Gln Glu Leu Val Val Ala Thr Gly Gly Ser Leu
        115                 120                 125 cat cgc aag ctg tgc gaa cag cct gaa ttg ctg gaa cat cgg gaa gat     432
His Arg Lys Leu Cys Glu Gln Pro Glu Leu Leu Glu His Arg Glu Asp
    130                 135                 140 ccc gaa ctg ccg gtg gaa cag caa tat gca ccg tcg cat gaa gtt cag     480
Pro Glu Leu Pro Val Glu Gln Gln Tyr Ala Pro Ser His Glu Val Gln
145                 150                 155                 160 gtt gaa gag ggg gga tta ctg tct gcg ttg tta cct gaa tgt agc aac     528
Val Glu Glu Gly Gly Leu Leu Ser Ala Leu Leu Pro Glu Cys Ser Asn
                165                 170                 175 ttt tgg gta aac tct cta cat gga caa ggg gcg aag gtc gtt agc cca     576
Phe Trp Val Asn Ser Leu His Gly Gln Gly Ala Lys Val Val Ser Pro
            180                 185                 190 cgg ttg cgt gtt gaa gct cgc tcg ccg gat ggc tta gtt gag gcg gtt     624
Arg Leu Arg Val Glu Ala Arg Ser Pro Asp Gly Leu Val Glu Ala Val
        195                 200                 205 agc gtc atc aat cat cct ttt gcg ctg ggc gta cag tgg cac ccg gaa     672
Ser Val Ile Asn His Pro Phe Ala Leu Gly Val Gln Trp His Pro Glu
    210                 215                 220 tgg aac agt agc gag tac gcg ctt tcg cgt ata ttg ttc gag ggc ttt     720
Trp Asn Ser Ser Glu Tyr Ala Leu Ser Arg Ile Leu Phe Glu Gly Phe
225                 230                 235                 240 atc acc gct tgt cag cac cat atc gct gaa aaa cag cga ctc tga         765
Ile Thr Ala Cys Gln His His Ile Ala Glu Lys Gln Arg Leu
                245                 250
```

<210> SEQ ID NO 4
<211> LENGTH: 254
<212> TYPE: PRT
<213> ORGANISM: Escherichia coli

<400> SEQUENCE: 4

```
Met Glu Asn Ile Met Asn Asn Pro Val Ile Gly Val Val Met Cys Arg
1               5                   10                  15
```

```
Asn Arg Leu Lys Gly His Ala Thr Gln Thr Leu Gln Glu Lys Tyr Leu
         20                  25                  30

Asn Ala Ile Ile His Ala Gly Gly Leu Pro Ile Ala Leu Pro His Ala
             35                  40                  45

Leu Ala Glu Pro Ser Leu Leu Glu Gln Leu Leu Pro Lys Leu Asp Gly
 50                  55                  60

Ile Tyr Leu Pro Gly Ser Pro Ser Asn Val Gln Pro His Leu Tyr Gly
 65                  70                  75                  80

Glu Asn Gly Asp Glu Pro Asp Ala Asp Pro Gly Arg Asp Leu Leu Ser
                 85                  90                  95

Met Ala Ile Ile Asn Ala Ala Leu Glu Arg Arg Ile Pro Ile Phe Ala
            100                 105                 110

Ile Cys Arg Gly Leu Gln Glu Leu Val Val Ala Thr Gly Gly Ser Leu
            115                 120                 125

His Arg Lys Leu Cys Glu Gln Pro Glu Leu Leu Glu His Arg Glu Asp
    130                 135                 140

Pro Glu Leu Pro Val Glu Gln Tyr Ala Pro Ser His Glu Val Gln
145                 150                 155                 160

Val Glu Glu Gly Gly Leu Leu Ser Ala Leu Leu Pro Glu Cys Ser Asn
                165                 170                 175

Phe Trp Val Asn Ser Leu His Gly Gln Gly Ala Lys Val Val Ser Pro
            180                 185                 190

Arg Leu Arg Val Glu Ala Arg Ser Pro Asp Gly Leu Val Glu Ala Val
        195                 200                 205

Ser Val Ile Asn His Pro Phe Ala Leu Gly Val Gln Trp His Pro Glu
    210                 215                 220

Trp Asn Ser Ser Glu Tyr Ala Leu Ser Arg Ile Leu Phe Glu Gly Phe
225                 230                 235                 240

Ile Thr Ala Cys Gln His His Ile Ala Glu Lys Gln Arg Leu
                245                 250
```

<210> SEQ ID NO 5  
<211> LENGTH: 558  
<212> TYPE: DNA  
<213> ORGANISM: Escherichia coli  
<220> FEATURE:  
<221> NAME/KEY: CDS  
<222> LOCATION: (1)..(558)

<400> SEQUENCE: 5

```
atg agt gat gag gga ctg gcg cca gga aaa cgc ttg tcg gaa atc cgc      48
Met Ser Asp Glu Gly Leu Ala Pro Gly Lys Arg Leu Ser Glu Ile Arg
1               5                  10                  15 cag cag cag ggg ctt tca caa cgt cgt gcc gcc gaa ctc tcc ggg ctg      96
Gln Gln Gln Gly Leu Ser Gln Arg Arg Ala Ala Glu Leu Ser Gly Leu
             20                  25                  30 act cac agt gct atc agt acg ata gaa caa gat aaa gtc agc cct gcc     144
Thr His Ser Ala Ile Ser Thr Ile Glu Gln Asp Lys Val Ser Pro Ala
         35                  40                  45 atc agt acg ctg caa aag ctg ctg aag gtg tat ggt ctg tca ctc tcg     192
Ile Ser Thr Leu Gln Lys Leu Leu Lys Val Tyr Gly Leu Ser Leu Ser
     50                  55                  60 gaa ttc ttt tcc gag ccg gaa aaa cct gat gag ccg cag gtc gtc att     240
Glu Phe Phe Ser Glu Pro Glu Lys Pro Asp Glu Pro Gln Val Val Ile
65                  70                  75                  80 aat cag gac gac tta att gag atg ggt agt cag ggt gtg tca atg aag     288
Asn Gln Asp Asp Leu Ile Glu Met Gly Ser Gln Gly Val Ser Met Lys
```

```
                     85                  90                  95
ctg gtt cat aac ggt aac ccg aat cgc acg ctg gcg atg atc ttt gaa      336
Leu Val His Asn Gly Asn Pro Asn Arg Thr Leu Ala Met Ile Phe Glu
            100                 105                 110 acg tac cag ccg ggc aca acc act ggg gaa aga att aag cat cag ggt      384
Thr Tyr Gln Pro Gly Thr Thr Thr Gly Glu Arg Ile Lys His Gln Gly
        115                 120                 125 gag gaa ata ggc act gta ctg gaa ggt gaa att gtt ctg acg att aat      432
Glu Glu Ile Gly Thr Val Leu Glu Gly Glu Ile Val Leu Thr Ile Asn
    130                 135                 140 ggt cag gat tac cac ctc gtc gcg ggg caa agt tat gcc att aat acc      480
Gly Gln Asp Tyr His Leu Val Ala Gly Gln Ser Tyr Ala Ile Asn Thr
145                 150                 155                 160 ggc atc ccg cac agt ttc agt aat acg tcg gca ggt att tgc cga att      528
Gly Ile Pro His Ser Phe Ser Asn Thr Ser Ala Gly Ile Cys Arg Ile
                165                 170                 175 atc agc gcc cat acg ccc acc acg ttt taa                              558
Ile Ser Ala His Thr Pro Thr Thr Phe
            180                 185

<210> SEQ ID NO 6
<211> LENGTH: 185
<212> TYPE: PRT
<213> ORGANISM: Escherichia coli

<400> SEQUENCE: 6

Met Ser Asp Glu Gly Leu Ala Pro Gly Lys Arg Leu Ser Glu Ile Arg
1               5                   10                  15

Gln Gln Gln Gly Leu Ser Gln Arg Arg Ala Ala Glu Leu Ser Gly Leu
            20                  25                  30

Thr His Ser Ala Ile Ser Thr Ile Glu Gln Asp Lys Val Ser Pro Ala
        35                  40                  45

Ile Ser Thr Leu Gln Lys Leu Leu Lys Val Tyr Gly Leu Ser Leu Ser
    50                  55                  60

Glu Phe Phe Ser Glu Pro Gly Lys Pro Asp Glu Pro Gln Val Val Ile
65              70                  75                  80

Asn Gln Asp Asp Leu Ile Glu Met Gly Ser Gln Gly Val Ser Met Lys
            85                  90                  95

Leu Val His Asn Gly Asn Pro Asn Arg Thr Leu Ala Met Ile Phe Glu
        100                 105                 110

Thr Tyr Gln Pro Gly Thr Thr Thr Gly Glu Arg Ile Lys His Gln Gly
    115                 120                 125

Glu Glu Ile Gly Thr Val Leu Glu Gly Glu Ile Val Leu Thr Ile Asn
130                 135                 140

Gly Gln Asp Tyr His Leu Val Ala Gly Gln Ser Tyr Ala Ile Asn Thr
145                 150                 155                 160

Gly Ile Pro His Ser Phe Ser Asn Thr Ser Ala Gly Ile Cys Arg Ile
                165                 170                 175

Ile Ser Ala His Thr Pro Thr Thr Phe
            180                 185

<210> SEQ ID NO 7
<211> LENGTH: 1488
<212> TYPE: DNA
<213> ORGANISM: Escherichia coli
<220> FEATURE:
<221> NAME/KEY: CDS
<222> LOCATION: (1)..(1488)
```

<400> SEQUENCE: 7

| | | | | | | | | | | | | | | | | |
|---|---|---|---|---|---|---|---|---|---|---|---|---|---|---|---|---|
| atg | aat | ttt | cat | cat | ctg | gct | tac | tgg | cag | gat | aaa | gcg | tta | agt | ctc | 48 |
| Met | Asn | Phe | His | His | Leu | Ala | Tyr | Trp | Gln | Asp | Lys | Ala | Leu | Ser | Leu | |
| 1 | | | | 5 | | | | | 10 | | | | | 15 | | |
| gcc | att | gaa | aac | cgc | tta | ttt | att | aac | ggt | gaa | tat | act | gct | gcg | gcg | 96 |
| Ala | Ile | Glu | Asn | Arg | Leu | Phe | Ile | Asn | Gly | Glu | Tyr | Thr | Ala | Ala | Ala | |
| | | | 20 | | | | | 25 | | | | | 30 | | | |
| gaa | aat | gaa | acc | ttt | gaa | acc | gtt | gat | ccg | gtc | acc | cag | gca | ccg | ctg | 144 |
| Glu | Asn | Glu | Thr | Phe | Glu | Thr | Val | Asp | Pro | Val | Thr | Gln | Ala | Pro | Leu | |
| | 35 | | | | | 40 | | | | | 45 | | | | | |
| gcg | aaa | att | gcc | cgc | ggc | aag | agc | gtc | gat | atc | gac | cgt | gcg | atg | agc | 192 |
| Ala | Lys | Ile | Ala | Arg | Gly | Lys | Ser | Val | Asp | Ile | Asp | Arg | Ala | Met | Ser | |
| 50 | | | | | 55 | | | | | 60 | | | | | | |
| gca | gca | cgc | ggc | gta | ttt | gaa | cgc | ggc | gac | tgg | tca | ctc | tct | tct | ccg | 240 |
| Ala | Ala | Arg | Gly | Val | Phe | Glu | Arg | Gly | Asp | Trp | Ser | Leu | Ser | Ser | Pro | |
| 65 | | | | 70 | | | | | 75 | | | | | 80 | | |
| gct | aaa | cgt | aaa | gcg | gta | ctg | aat | aaa | ctc | gcc | gat | tta | atg | gaa | gcc | 288 |
| Ala | Lys | Arg | Lys | Ala | Val | Leu | Asn | Lys | Leu | Ala | Asp | Leu | Met | Glu | Ala | |
| | | | 85 | | | | | 90 | | | | | 95 | | | |
| cac | gcc | gaa | gag | ctg | gca | ctg | ctg | gaa | act | ctc | gac | acc | ggc | aaa | ccg | 336 |
| His | Ala | Glu | Glu | Leu | Ala | Leu | Leu | Glu | Thr | Leu | Asp | Thr | Gly | Lys | Pro | |
| | | 100 | | | | | 105 | | | | | 110 | | | | |
| att | cgt | cac | agt | ctg | cgt | gat | gat | att | ccc | ggc | gcg | gcg | cgc | gcc | att | 384 |
| Ile | Arg | His | Ser | Leu | Arg | Asp | Asp | Ile | Pro | Gly | Ala | Ala | Arg | Ala | Ile | |
| | 115 | | | | | 120 | | | | | 125 | | | | | |
| cgc | tgg | tac | gcc | gaa | gcg | atc | gac | aaa | gtg | tat | ggc | gaa | gtg | gcg | acc | 432 |
| Arg | Trp | Tyr | Ala | Glu | Ala | Ile | Asp | Lys | Val | Tyr | Gly | Glu | Val | Ala | Thr | |
| 130 | | | | | 135 | | | | | 140 | | | | | | |
| acc | agt | agc | cat | gag | ctg | gcg | atg | atc | gtg | cgt | gaa | ccg | gtc | ggc | gtg | 480 |
| Thr | Ser | Ser | His | Glu | Leu | Ala | Met | Ile | Val | Arg | Glu | Pro | Val | Gly | Val | |
| 145 | | | | | 150 | | | | | 155 | | | | | 160 | |
| att | gcc | gcc | atc | gtg | ccg | tgg | aac | ttc | ccg | ctg | ttg | ctg | act | tgc | tgg | 528 |
| Ile | Ala | Ala | Ile | Val | Pro | Trp | Asn | Phe | Pro | Leu | Leu | Leu | Thr | Cys | Trp | |
| | | | 165 | | | | | 170 | | | | | 175 | | | |
| aaa | ctc | ggc | ccg | gcg | ctg | gcg | gcg | gga | aac | agc | gtg | att | cta | aaa | ccg | 576 |
| Lys | Leu | Gly | Pro | Ala | Leu | Ala | Ala | Gly | Asn | Ser | Val | Ile | Leu | Lys | Pro | |
| | | | | 180 | | | | | 185 | | | | | 190 | | |
| tct | gaa | aaa | tca | ccg | ctc | agt | gcg | att | cgt | ctc | gcg | ggg | ctg | gcg | aaa | 624 |
| Ser | Glu | Lys | Ser | Pro | Leu | Ser | Ala | Ile | Arg | Leu | Ala | Gly | Leu | Ala | Lys | |
| | | 195 | | | | | 200 | | | | | 205 | | | | |
| gaa | gca | ggc | ttg | ccg | gat | ggt | gtg | ttg | aac | gtg | gtg | acg | ggt | ttt | ggt | 672 |
| Glu | Ala | Gly | Leu | Pro | Asp | Gly | Val | Leu | Asn | Val | Val | Thr | Gly | Phe | Gly | |
| | 210 | | | | | 215 | | | | | 220 | | | | | |
| cat | gaa | gcc | ggg | cag | gcg | ctg | tcg | cgt | cat | aac | gat | atc | gac | gcc | att | 720 |
| His | Glu | Ala | Gly | Gln | Ala | Leu | Ser | Arg | His | Asn | Asp | Ile | Asp | Ala | Ile | |
| 225 | | | | | 230 | | | | | 235 | | | | | 240 | |
| gcc | ttt | acc | ggt | tca | acc | cgt | acc | ggg | aaa | cag | ctg | ctg | aaa | gat | gcg | 768 |
| Ala | Phe | Thr | Gly | Ser | Thr | Arg | Thr | Gly | Lys | Gln | Leu | Leu | Lys | Asp | Ala | |
| | | | 245 | | | | | 250 | | | | | 255 | | | |
| ggc | gac | agc | aac | atg | aaa | cgc | gtc | tgg | ctg | gaa | gcg | ggc | ggc | aaa | agc | 816 |
| Gly | Asp | Ser | Asn | Met | Lys | Arg | Val | Trp | Leu | Glu | Ala | Gly | Gly | Lys | Ser | |
| | | | | 260 | | | | | 265 | | | | | 270 | | |
| gcc | aac | atc | gtt | ttc | gct | gac | tgc | ccg | gat | ttg | caa | cag | gcg | gca | agc | 864 |
| Ala | Asn | Ile | Val | Phe | Ala | Asp | Cys | Pro | Asp | Leu | Gln | Gln | Ala | Ala | Ser | |
| | | 275 | | | | | 280 | | | | | 285 | | | | |
| gcc | acc | gca | gca | ggc | att | ttc | tac | aac | cag | gga | cag | gtg | tgc | atc | gcc | 912 |
| Ala | Thr | Ala | Ala | Gly | Ile | Phe | Tyr | Asn | Gln | Gly | Gln | Val | Cys | Ile | Ala | |
| | 290 | | | | | 295 | | | | | 300 | | | | | |
| gga | acg | cgc | ctg | ttg | ctg | gaa | gag | agc | atc | gcc | gat | gaa | ttc | tta | gcc | 960 |

```
                Gly Thr Arg Leu Leu Leu Glu Glu Ser Ile Ala Asp Glu Phe Leu Ala
                305                 310                 315                 320 ctg tta aaa cag cag gcg caa aac tgg cag ccg ggc cat cca ctt gat         1008
Leu Leu Lys Gln Gln Ala Gln Asn Trp Gln Pro Gly His Pro Leu Asp
                325                 330                 335 ccc gca acc acc atg ggc acc tta atc gac tgc gcc cac gcc gac tcg         1056
Pro Ala Thr Thr Met Gly Thr Leu Ile Asp Cys Ala His Ala Asp Ser
            340                 345                 350 gtc cat agc ttt att cgg gaa ggc gaa agc aaa ggg caa ctg ttg ttg         1104
Val His Ser Phe Ile Arg Glu Gly Glu Ser Lys Gly Gln Leu Leu Leu
        355                 360                 365 gat ggc cgt aac gcc ggg ctg gct gcc gcc atc ggc ccg acc atc ttt         1152
Asp Gly Arg Asn Ala Gly Leu Ala Ala Ala Ile Gly Pro Thr Ile Phe
    370                 375                 380 gtg gat gtg gac ccg aat gcg tcc tta agt cgc gaa gag att ttc ggt         1200
Val Asp Val Asp Pro Asn Ala Ser Leu Ser Arg Glu Glu Ile Phe Gly
385                 390                 395                 400 ccg gtg ctg gtg gtc acg cgt ttc aca tca gaa gaa cag gcg cta cag         1248
Pro Val Leu Val Val Thr Arg Phe Thr Ser Glu Glu Gln Ala Leu Gln
                405                 410                 415 ctt gcc aac gac agc cag tac ggc ctt ggc gcg gcg gta tgg acg cgc         1296
Leu Ala Asn Asp Ser Gln Tyr Gly Leu Gly Ala Ala Val Trp Thr Arg
            420                 425                 430 gac ctc tcc cgc gcg cac cgc atg agc cga cgc ctg aaa gcc ggt tcc         1344
Asp Leu Ser Arg Ala His Arg Met Ser Arg Arg Leu Lys Ala Gly Ser
        435                 440                 445 gtc ttc gtc aat aac tac aac gac ggc gat atg acc gtg ccg ttt ggc         1392
Val Phe Val Asn Asn Tyr Asn Asp Gly Asp Met Thr Val Pro Phe Gly
    450                 455                 460 ggc tat aag cag agc ggc aac ggt cgc gac aaa tcc ctg cat gcc ctt         1440
Gly Tyr Lys Gln Ser Gly Asn Gly Arg Asp Lys Ser Leu His Ala Leu
465                 470                 475                 480 gaa aaa ttc act gaa ctg aaa acc atc tgg ata agc ctg gag gcc tga         1488
Glu Lys Phe Thr Glu Leu Lys Thr Ile Trp Ile Ser Leu Glu Ala
                485                 490                 495

<210> SEQ ID NO 8
<211> LENGTH: 495
<212> TYPE: PRT
<213> ORGANISM: Escherichia coli

<400> SEQUENCE: 8

Met Asn Phe His His Leu Ala Tyr Trp Gln Asp Lys Ala Leu Ser Leu
1               5                   10                  15

Ala Ile Glu Asn Arg Leu Phe Ile Asn Gly Glu Tyr Thr Ala Ala
            20                  25                  30

Glu Asn Glu Thr Phe Glu Thr Val Asp Pro Val Thr Gln Ala Pro Leu
        35                  40                  45

Ala Lys Ile Ala Arg Gly Lys Ser Val Asp Ile Asp Arg Ala Met Ser
    50                  55                  60

Ala Ala Arg Gly Val Phe Glu Arg Gly Asp Trp Ser Leu Ser Ser Pro
65                  70                  75                  80

Ala Lys Arg Lys Ala Val Leu Asn Lys Leu Ala Asp Leu Met Glu Ala
                85                  90                  95

His Ala Glu Glu Leu Ala Leu Leu Glu Thr Leu Asp Thr Gly Lys Pro
            100                 105                 110

Ile Arg His Ser Leu Arg Asp Asp Ile Pro Gly Ala Ala Arg Ala Ile
        115                 120                 125
```

```
Arg Trp Tyr Ala Glu Ala Ile Asp Lys Val Tyr Gly Glu Val Ala Thr
            130                 135                 140

Thr Ser Ser His Glu Leu Ala Met Ile Val Arg Glu Pro Val Gly Val
145                 150                 155                 160

Ile Ala Ala Ile Val Pro Trp Asn Phe Pro Leu Leu Leu Thr Cys Trp
                165                 170                 175

Lys Leu Gly Pro Ala Leu Ala Ala Gly Asn Ser Val Ile Leu Lys Pro
            180                 185                 190

Ser Glu Lys Ser Pro Leu Ser Ala Ile Arg Leu Ala Gly Leu Ala Lys
        195                 200                 205

Glu Ala Gly Leu Pro Asp Gly Val Leu Asn Val Thr Gly Phe Gly
210                 215                 220

His Glu Ala Gly Gln Ala Leu Ser Arg His Asn Asp Ile Asp Ala Ile
225                 230                 235                 240

Ala Phe Thr Gly Ser Thr Arg Thr Gly Lys Gln Leu Leu Lys Asp Ala
                245                 250                 255

Gly Asp Ser Asn Met Lys Arg Val Trp Leu Glu Ala Gly Gly Lys Ser
            260                 265                 270

Ala Asn Ile Val Phe Ala Asp Cys Pro Asp Leu Gln Gln Ala Ala Ser
        275                 280                 285

Ala Thr Ala Ala Gly Ile Phe Tyr Asn Gln Gly Gln Val Cys Ile Ala
    290                 295                 300

Gly Thr Arg Leu Leu Leu Glu Glu Ser Ile Ala Asp Glu Phe Leu Ala
305                 310                 315                 320

Leu Leu Lys Gln Gln Ala Gln Asn Trp Gln Pro Gly His Pro Leu Asp
                325                 330                 335

Pro Ala Thr Thr Met Gly Thr Leu Ile Asp Cys Ala His Ala Asp Ser
            340                 345                 350

Val His Ser Phe Ile Arg Glu Gly Glu Ser Lys Gly Gln Leu Leu Leu
        355                 360                 365

Asp Gly Arg Asn Ala Gly Leu Ala Ala Ala Ile Gly Pro Thr Ile Phe
    370                 375                 380

Val Asp Val Asp Pro Asn Ala Ser Leu Ser Arg Glu Glu Ile Phe Gly
385                 390                 395                 400

Pro Val Leu Val Val Thr Arg Phe Thr Ser Glu Glu Gln Ala Leu Gln
                405                 410                 415

Leu Ala Asn Asp Ser Gln Tyr Gly Leu Gly Ala Ala Val Trp Thr Arg
            420                 425                 430

Asp Leu Ser Arg Ala His Arg Met Ser Arg Arg Leu Lys Ala Gly Ser
        435                 440                 445

Val Phe Val Asn Asn Tyr Asn Asp Gly Asp Met Thr Val Pro Phe Gly
    450                 455                 460

Gly Tyr Lys Gln Ser Gly Asn Gly Arg Asp Lys Ser Leu His Ala Leu
465                 470                 475                 480

Glu Lys Phe Thr Glu Leu Lys Thr Ile Trp Ile Ser Leu Glu Ala
                485                 490                 495

<210> SEQ ID NO 9
<211> LENGTH: 1281
<212> TYPE: DNA
<213> ORGANISM: Escherichia coli
<220> FEATURE:
<221> NAME/KEY: CDS
<222> LOCATION: (1)..(1281)

<400> SEQUENCE: 9
```

```
atg acc gaa cat acc agc agt tac tac gcc gcc agt gcg aat aaa tat        48
Met Thr Glu His Thr Ser Ser Tyr Tyr Ala Ala Ser Ala Asn Lys Tyr
1               5                   10                  15 gca cca ttc gac acg ctg aat gag tca atc acc tgc gac gtt tgc gtg        96
Ala Pro Phe Asp Thr Leu Asn Glu Ser Ile Thr Cys Asp Val Cys Val
            20                  25                  30 gtt ggc ggc ggc tat acc ggg ctc tcc tcc gcg ctg cat ctg gcg gaa       144
Val Gly Gly Gly Tyr Thr Gly Leu Ser Ser Ala Leu His Leu Ala Glu
        35                  40                  45 gcg ggc ttt gac gta gtg gtt ctc gaa gcc tca cgc atc ggc ttt ggc       192
Ala Gly Phe Asp Val Val Val Leu Glu Ala Ser Arg Ile Gly Phe Gly
    50                  55                  60 gca agc ggg cgc aat ggc gga cag ctt gtg aac tcc tac agc cgc gac       240
Ala Ser Gly Arg Asn Gly Gly Gln Leu Val Asn Ser Tyr Ser Arg Asp
65              70                  75                  80 atc gac gtg atc gaa aaa agc tac ggc atg gac acc gcc cgt atg ctc       288
Ile Asp Val Ile Glu Lys Ser Tyr Gly Met Asp Thr Ala Arg Met Leu
                85                  90                  95 ggc agc atg atg ttc gaa ggt ggt gag atc atc cgc gaa cgt atc aaa       336
Gly Ser Met Met Phe Glu Gly Gly Glu Ile Ile Arg Glu Arg Ile Lys
            100                 105                 110 cgt tat cag att gac tgc gac tac cgc ccc ggc ggc ctg ttt gtg gcg       384
Arg Tyr Gln Ile Asp Cys Asp Tyr Arg Pro Gly Gly Leu Phe Val Ala
        115                 120                 125 atg aat gat aaa cag ctc gcc aca ctt gaa gag cag aaa gag aac tgg       432
Met Asn Asp Lys Gln Leu Ala Thr Leu Glu Glu Gln Lys Glu Asn Trp
    130                 135                 140 gaa cgc tac ggc aat aaa cag ctg gaa ttg ctg gac gcc aac gcc att       480
Glu Arg Tyr Gly Asn Lys Gln Leu Glu Leu Leu Asp Ala Asn Ala Ile
145                 150                 155                 160 cgc cgt gaa gta gcc agc gat cgc tat acc ggt gcg ctg ctg gat cac       528
Arg Arg Glu Val Ala Ser Asp Arg Tyr Thr Gly Ala Leu Leu Asp His
                165                 170                 175 agc ggt ggg cat att cat ccg cta aac ctt gcc att ggc gaa gcg gac       576
Ser Gly Gly His Ile His Pro Leu Asn Leu Ala Ile Gly Glu Ala Asp
            180                 185                 190 gcc atc cgc ctc aac ggc ggg cgc gtg tat gaa ctt tct gcc gtg acg       624
Ala Ile Arg Leu Asn Gly Gly Arg Val Tyr Glu Leu Ser Ala Val Thr
        195                 200                 205 cag atc cag cac acc acg cca gcc gtt gtg cga act gcc aaa ggt cag       672
Gln Ile Gln His Thr Thr Pro Ala Val Val Arg Thr Ala Lys Gly Gln
    210                 215                 220 gtg acg gcg aag tat gtg att gtc gcc ggg aat gcg tat ctg ggc gat       720
Val Thr Ala Lys Tyr Val Ile Val Ala Gly Asn Ala Tyr Leu Gly Asp
225                 230                 235                 240 aaa gta gag ccg gaa ctg gcg aaa cgc agc atg ccg tgc ggc acg cag       768
Lys Val Glu Pro Glu Leu Ala Lys Arg Ser Met Pro Cys Gly Thr Gln
                245                 250                 255 gtg atc acc acc gaa cgg ctg tcg gaa gat tta gcc cgt tcg ctg atc       816
Val Ile Thr Thr Glu Arg Leu Ser Glu Asp Leu Ala Arg Ser Leu Ile
            260                 265                 270 ccg aaa aac tac tgt gtg gaa gac tgt aac tat ctg ctt gat tac tac       864
Pro Lys Asn Tyr Cys Val Glu Asp Cys Asn Tyr Leu Leu Asp Tyr Tyr
        275                 280                 285 cgt ctt acc gcc gac aac cgc ctg ctg tac ggc ggc ggc gtg gtc tac       912
Arg Leu Thr Ala Asp Asn Arg Leu Leu Tyr Gly Gly Gly Val Val Tyr
    290                 295                 300 ggc gcg cgc gac ccg gat gac gtt gag cgc ctt gtg gtg ccg aaa ctg       960
Gly Ala Arg Asp Pro Asp Asp Val Glu Arg Leu Val Val Pro Lys Leu
```

```
                    305                 310                 315                 320
ctg aaa acc ttc ccg cag ctg aag ggc gtg aaa att gat tac cgc tgg        1008
Leu Lys Thr Phe Pro Gln Leu Lys Gly Val Lys Ile Asp Tyr Arg Trp
                325                 330                 335 acg ggc aac ttc ctg ctg acc ctg tcg cgt atg ccg cag ttt ggt cgc        1056
Thr Gly Asn Phe Leu Leu Thr Leu Ser Arg Met Pro Gln Phe Gly Arg
        340                 345                 350 ctc gat acc aac atc tat tac atg cag ggc tac agc ggc cac ggc gtg        1104
Leu Asp Thr Asn Ile Tyr Tyr Met Gln Gly Tyr Ser Gly His Gly Val
            355                 360                 365 acc tgt act cat cta gcc gga cgt ttg att gcc gaa ctg ctg cgc ggc        1152
Thr Cys Thr His Leu Ala Gly Arg Leu Ile Ala Glu Leu Leu Arg Gly
    370                 375                 380 gac gcc gaa cgt ttc gat gcc ttc gcc aat ctg ccg cat tac ccg ttc        1200
Asp Ala Glu Arg Phe Asp Ala Phe Ala Asn Leu Pro His Tyr Pro Phe
385                 390                 395                 400 ccc ggg cgc acg ctg cgt gtg ccg ttt acc gcg atg ggc gcg gcg            1248
Pro Gly Gly Arg Thr Leu Arg Val Pro Phe Thr Ala Met Gly Ala Ala
                405                 410                 415 tat tac agc ctg cgc gat cgt ctg ggc gtt taa                            1281
Tyr Tyr Ser Leu Arg Asp Arg Leu Gly Val
                420                 425

<210> SEQ ID NO 10
<211> LENGTH: 426
<212> TYPE: PRT
<213> ORGANISM: Escherichia coli

<400> SEQUENCE: 10

Met Thr Glu His Thr Ser Ser Tyr Tyr Ala Ala Ser Ala Asn Lys Tyr
1               5                   10                  15

Ala Pro Phe Asp Thr Leu Asn Glu Ser Ile Thr Cys Asp Val Cys Val
                20                  25                  30

Val Gly Gly Gly Tyr Thr Gly Leu Ser Ser Ala Leu His Leu Ala Glu
        35                  40                  45

Ala Gly Phe Asp Val Val Leu Glu Ala Ser Arg Ile Gly Phe Gly
    50                  55                  60

Ala Ser Gly Arg Asn Gly Gly Gln Leu Val Asn Ser Tyr Ser Arg Asp
65                  70                  75                  80

Ile Asp Val Ile Glu Lys Ser Tyr Gly Met Asp Thr Ala Arg Met Leu
                85                  90                  95

Gly Ser Met Met Phe Glu Gly Gly Glu Ile Ile Arg Glu Arg Ile Lys
            100                 105                 110

Arg Tyr Gln Ile Asp Cys Asp Tyr Arg Pro Gly Gly Leu Phe Val Ala
        115                 120                 125

Met Asn Asp Lys Gln Leu Ala Thr Leu Glu Glu Lys Glu Asn Trp
    130                 135                 140

Glu Arg Tyr Gly Asn Lys Gln Leu Glu Leu Leu Asp Ala Asn Ala Ile
145                 150                 155                 160

Arg Arg Glu Val Ala Ser Asp Arg Tyr Thr Gly Ala Leu Leu Asp His
                165                 170                 175

Ser Gly Gly His Ile His Pro Leu Asn Leu Ala Ile Gly Glu Ala Asp
            180                 185                 190

Ala Ile Arg Leu Asn Gly Gly Arg Val Tyr Glu Leu Ser Ala Val Thr
        195                 200                 205

Gln Ile Gln His Thr Thr Pro Ala Val Val Arg Thr Ala Lys Gly Gln
    210                 215                 220
```

```
Val Thr Ala Lys Tyr Val Ile Val Ala Gly Asn Ala Tyr Leu Gly Asp
225                 230                 235                 240

Lys Val Glu Pro Glu Leu Ala Lys Arg Ser Met Pro Cys Gly Thr Gln
            245                 250                 255

Val Ile Thr Thr Glu Arg Leu Ser Glu Asp Leu Ala Arg Ser Leu Ile
        260                 265                 270

Pro Lys Asn Tyr Cys Val Glu Asp Cys Asn Tyr Leu Leu Asp Tyr Tyr
            275                 280                 285

Arg Leu Thr Ala Asp Asn Arg Leu Leu Tyr Gly Gly Val Val Tyr
        290                 295                 300

Gly Ala Arg Asp Pro Asp Val Glu Arg Leu Val Val Pro Lys Leu
305                 310                 315                 320

Leu Lys Thr Phe Pro Gln Leu Lys Gly Val Lys Ile Asp Tyr Arg Trp
            325                 330                 335

Thr Gly Asn Phe Leu Leu Thr Leu Ser Arg Met Pro Gln Phe Gly Arg
        340                 345                 350

Leu Asp Thr Asn Ile Tyr Tyr Met Gln Gly Tyr Ser Gly His Gly Val
        355                 360                 365

Thr Cys Thr His Leu Ala Gly Arg Leu Ile Ala Glu Leu Leu Arg Gly
        370                 375                 380

Asp Ala Glu Arg Phe Asp Ala Phe Ala Asn Leu Pro His Tyr Pro Phe
385                 390                 395                 400

Pro Gly Gly Arg Thr Leu Arg Val Pro Phe Thr Ala Met Gly Ala Ala
            405                 410                 415

Tyr Tyr Ser Leu Arg Asp Arg Leu Gly Val
            420                 425

<210> SEQ ID NO 11
<211> LENGTH: 1266
<212> TYPE: DNA
<213> ORGANISM: Escherichia coli
<220> FEATURE:
<221> NAME/KEY: CDS
<222> LOCATION: (1)..(1266)

<400> SEQUENCE: 11 atg agc aac aat gaa ttc cat cag cgt cgt ctt tct gcc act ccg cgc    48
Met Ser Asn Asn Glu Phe His Gln Arg Arg Leu Ser Ala Thr Pro Arg
1               5                   10                  15 ggg gtt ggc gtg atg tgt aac ttc ttc gcc cag tcg gct gaa aac gcc    96
Gly Val Gly Val Met Cys Asn Phe Phe Ala Gln Ser Ala Glu Asn Ala
            20                  25                  30 acg ctg aag gat gtt gag ggc aac gag tac atc gat ttc gcc gca ggc   144
Thr Leu Lys Asp Val Glu Gly Asn Glu Tyr Ile Asp Phe Ala Ala Gly
        35                  40                  45 att gcg gtg ctg aat acc gga cat cgc cac cct gat ctg gtc gcg gcg   192
Ile Ala Val Leu Asn Thr Gly His Arg His Pro Asp Leu Val Ala Ala
    50                  55                  60 gtg gag cag caa ctg caa cag ttt acc cac acc gcg tat cag att gtg   240
Val Glu Gln Gln Leu Gln Gln Phe Thr His Thr Ala Tyr Gln Ile Val
65                  70                  75                  80 ccg tat gaa agc tac gtc acc ctg gcg gag aaa atc aac gcc ctt gcc   288
Pro Tyr Glu Ser Tyr Val Thr Leu Ala Glu Lys Ile Asn Ala Leu Ala
            85                  90                  95 ccg gtg agc ggg cag gcc aaa acc gcg ttc ttc acc acc ggt gcg gaa   336
Pro Val Ser Gly Gln Ala Lys Thr Ala Phe Phe Thr Thr Gly Ala Glu
            100                 105                 110
```

```
gcg gtg gaa aac gcg gtg aaa att gct cgc gcc cat acc gga cgc cct      384
Ala Val Glu Asn Ala Val Lys Ile Ala Arg Ala His Thr Gly Arg Pro
        115                 120                 125 ggc gtg att gcg ttt agc ggc ggc ttt cac ggt cgt acg tat atg acc      432
Gly Val Ile Ala Phe Ser Gly Gly Phe His Gly Arg Thr Tyr Met Thr
    130                 135                 140 atg gcg ctg acc gga aaa gtt gcg ccg tac aaa atc ggc ttc ggc ccg      480
Met Ala Leu Thr Gly Lys Val Ala Pro Tyr Lys Ile Gly Phe Gly Pro
145                 150                 155                 160 ttc cct ggt tcg gtg tat cac gta cct tat ccg tca gat tta cac ggc      528
Phe Pro Gly Ser Val Tyr His Val Pro Tyr Pro Ser Asp Leu His Gly
                165                 170                 175 att tca aca cag gac tcc ctc gac gcc atc gaa cgc ttg ttt aaa tca      576
Ile Ser Thr Gln Asp Ser Leu Asp Ala Ile Glu Arg Leu Phe Lys Ser
            180                 185                 190 gac atc gaa gcg aag cag gtg gcg gcg att att ttc gaa ccg gtg cag      624
Asp Ile Glu Ala Lys Gln Val Ala Ala Ile Ile Phe Glu Pro Val Gln
        195                 200                 205 ggc gag ggc ggt ttc aac gtt gcg cca aaa gag ctg gtt gcc gct att      672
Gly Glu Gly Gly Phe Asn Val Ala Pro Lys Glu Leu Val Ala Ala Ile
    210                 215                 220 cgc cgc ctg tgc gac gag cac ggt att gtg atg att gct gat gaa gtg      720
Arg Arg Leu Cys Asp Glu His Gly Ile Val Met Ile Ala Asp Glu Val
225                 230                 235                 240 caa agc ggc ttt gcg cgt acc ggt aag ctg ttt gcc atg gat cat tac      768
Gln Ser Gly Phe Ala Arg Thr Gly Lys Leu Phe Ala Met Asp His Tyr
                245                 250                 255 gcc gat aag ccg gat tta atg acg atg gcg aaa agc ctc gcg ggc ggg      816
Ala Asp Lys Pro Asp Leu Met Thr Met Ala Lys Ser Leu Ala Gly Gly
            260                 265                 270 atg ccg ctt tcg ggc gtg gtc ggt aac gcg aat att atg gac gca ccc      864
Met Pro Leu Ser Gly Val Val Gly Asn Ala Asn Ile Met Asp Ala Pro
        275                 280                 285 gcg ccg ggc ggg ctt ggc ggc acc tac gcc ggt aac ccg ctg gcg gtg      912
Ala Pro Gly Gly Leu Gly Gly Thr Tyr Ala Gly Asn Pro Leu Ala Val
    290                 295                 300 gct gcc gcg cac gcg gtg ctc aac att atc gac aaa gaa tca ctc tgc      960
Ala Ala Ala His Ala Val Leu Asn Ile Ile Asp Lys Glu Ser Leu Cys
305                 310                 315                 320 gaa cgc gcg aat caa ctg ggc cag cgt ctc aaa aac acg ttg att gat     1008
Glu Arg Ala Asn Gln Leu Gly Gln Arg Leu Lys Asn Thr Leu Ile Asp
                325                 330                 335 gcc aaa gaa agc gtt ccg gcc att gct gcg gta cgc ggc ctg ggg tcg     1056
Ala Lys Glu Ser Val Pro Ala Ile Ala Ala Val Arg Gly Leu Gly Ser
            340                 345                 350 atg att gcg gta gag ttt aac gat ccg caa acg ggc gag ccg tca gcg     1104
Met Ile Ala Val Glu Phe Asn Asp Pro Gln Thr Gly Glu Pro Ser Ala
        355                 360                 365 gcg att gca cag aaa atc cag caa cgc gcg ctg gcg cag ggg ctg ctc     1152
Ala Ile Ala Gln Lys Ile Gln Gln Arg Ala Leu Ala Gln Gly Leu Leu
    370                 375                 380 ctg ctg acc tgt ggc gca tac ggc aac gtg att cgc ttc ctg tat ccg     1200
Leu Leu Thr Cys Gly Ala Tyr Gly Asn Val Ile Arg Phe Leu Tyr Pro
385                 390                 395                 400 ctg acc atc ccg gat gcg caa ttc gat gcg gca atg aaa att ttg cag     1248
Leu Thr Ile Pro Asp Ala Gln Phe Asp Ala Ala Met Lys Ile Leu Gln
                405                 410                 415 gat gcg ctg agc gat taa                                             1266
Asp Ala Leu Ser Asp
            420
```

<210> SEQ ID NO 12
<211> LENGTH: 421
<212> TYPE: PRT
<213> ORGANISM: Escherichia coli

<400> SEQUENCE: 12

```
Met Ser Asn Asn Glu Phe His Gln Arg Arg Leu Ser Ala Thr Pro Arg
1               5                   10                  15

Gly Val Gly Val Met Cys Asn Phe Ala Gln Ser Ala Glu Asn Ala
            20                  25                  30

Thr Leu Lys Asp Val Glu Gly Asn Glu Tyr Ile Asp Phe Ala Ala Gly
        35                  40                  45

Ile Ala Val Leu Asn Thr Gly His Arg His Pro Asp Leu Val Ala Ala
    50                  55                  60

Val Glu Gln Gln Leu Gln Gln Phe Thr His Thr Ala Tyr Gln Ile Val
65                  70                  75                  80

Pro Tyr Glu Ser Tyr Val Thr Leu Ala Glu Lys Ile Asn Ala Leu Ala
                85                  90                  95

Pro Val Ser Gly Gln Ala Lys Thr Ala Phe Phe Thr Thr Gly Ala Glu
            100                 105                 110

Ala Val Glu Asn Ala Val Lys Ile Ala Arg Ala His Thr Gly Arg Pro
        115                 120                 125

Gly Val Ile Ala Phe Ser Gly Phe His Gly Arg Thr Tyr Met Thr
    130                 135                 140

Met Ala Leu Thr Gly Lys Val Ala Pro Tyr Lys Ile Gly Phe Gly Pro
145                 150                 155                 160

Phe Pro Gly Ser Val Tyr His Val Pro Tyr Pro Ser Asp Leu His Gly
                165                 170                 175

Ile Ser Thr Gln Asp Ser Leu Asp Ala Ile Glu Arg Leu Phe Lys Ser
            180                 185                 190

Asp Ile Glu Ala Lys Gln Val Ala Ala Ile Ile Phe Glu Pro Val Gln
        195                 200                 205

Gly Glu Gly Gly Phe Asn Val Ala Pro Lys Glu Leu Val Ala Ala Ile
    210                 215                 220

Arg Arg Leu Cys Asp Glu His Gly Ile Val Met Ile Ala Asp Glu Val
225                 230                 235                 240

Gln Ser Gly Phe Ala Arg Thr Gly Lys Leu Phe Ala Met Asp His Tyr
                245                 250                 255

Ala Asp Lys Pro Asp Leu Met Thr Met Ala Lys Ser Leu Ala Gly Gly
            260                 265                 270

Met Pro Leu Ser Gly Val Val Gly Asn Ala Asn Ile Met Asp Ala Pro
        275                 280                 285

Ala Pro Gly Gly Leu Gly Gly Thr Tyr Ala Gly Asn Pro Leu Ala Val
    290                 295                 300

Ala Ala His Ala Val Leu Asn Ile Ile Asp Lys Glu Ser Leu Cys
305                 310                 315                 320

Glu Arg Ala Asn Gln Leu Gly Gln Arg Leu Lys Asn Thr Leu Ile Asp
                325                 330                 335

Ala Lys Glu Ser Val Pro Ala Ile Ala Ala Val Arg Gly Leu Gly Ser
            340                 345                 350

Met Ile Ala Val Glu Phe Asn Asp Pro Gln Thr Gly Glu Pro Ser Ala
        355                 360                 365

Ala Ile Ala Gln Lys Ile Gln Gln Arg Ala Leu Ala Gln Gly Leu Leu
```

```
                370             375             380
Leu Leu Thr Cys Gly Ala Tyr Gly Asn Val Ile Arg Phe Leu Tyr Pro
385             390             395             400

Leu Thr Ile Pro Asp Ala Gln Phe Asp Ala Ala Met Lys Ile Leu Gln
            405             410             415

Asp Ala Leu Ser Asp
        420
```

```
<210> SEQ ID NO 13
<211> LENGTH: 64
<212> TYPE: DNA
<213> ORGANISM: Artificial Sequence
<220> FEATURE:
<223> OTHER INFORMATION: Primer P1

<400> SEQUENCE: 13
cgctcaggcc gatgaaacaa ccccgcaagg ggtattcgct caagttagta taaaaaagct    60
gaac                                                                 64

<210> SEQ ID NO 14
<211> LENGTH: 64
<212> TYPE: DNA
<213> ORGANISM: Artificial Sequence
<220> FEATURE:
<223> OTHER INFORMATION: Primer P2

<400> SEQUENCE: 14
taagcgcagc gcatcagaca ttattgcgtt gggctatgaa gcctgctttt ttatactaag    60
ttgg                                                                 64

<210> SEQ ID NO 15
<211> LENGTH: 64
<212> TYPE: DNA
<213> ORGANISM: Artificial Sequence
<220> FEATURE:
<223> OTHER INFORMATION: Primer P3

<400> SEQUENCE: 15
taattcaata agtggcgttc gccatgcgag gataaacgct caagttagta taaaaaagct    60
gaac                                                                 64

<210> SEQ ID NO 16
<211> LENGTH: 64
<212> TYPE: DNA
<213> ORGANISM: Artificial Sequence
<220> FEATURE:
<223> OTHER INFORMATION: Primer P4

<400> SEQUENCE: 16
gggtgagggc accaacgcgc agcggaccca atcacttgaa gcctgctttt ttatactaag    60
ttgg                                                                 64

<210> SEQ ID NO 17
<211> LENGTH: 64
<212> TYPE: DNA
<213> ORGANISM: Artificial Sequence
<220> FEATURE:
<223> OTHER INFORMATION: Primer P5

<400> SEQUENCE: 17
ttagccgcga agctgaaagc cgataagaaa agcggtcgct caagttagta taaaaaagct    60
```

```
gaac                                                                  64

<210> SEQ ID NO 18
<211> LENGTH: 64
<212> TYPE: DNA
<213> ORGANISM: Artificial Sequence
<220> FEATURE:
<223> OTHER INFORMATION: Primer P6

<400> SEQUENCE: 18
gacctcatca gtgacttcca taccgccatg taggcctgaa gcctgctttt ttatactaag    60
ttgg                                                                  64

<210> SEQ ID NO 19
<211> LENGTH: 64
<212> TYPE: DNA
<213> ORGANISM: Artificial Sequence
<220> FEATURE:
<223> OTHER INFORMATION: Primer P7

<400> SEQUENCE: 19
cgctcaggcc gatgaaacaa ccccgcaagg ggtatttgaa gcctgccttt ttatactaag    60
ttgg                                                                  64

<210> SEQ ID NO 20
<211> LENGTH: 66
<212> TYPE: DNA
<213> ORGANISM: Artificial Sequence
<220> FEATURE:
<223> OTHER INFORMATION: Primer P8

<400> SEQUENCE: 20
ttttgcaaac tcaatttaac atttgacaaa catttagtcg ctcaagttag tataaaaag     60 ctgaac                                                                66
```

METHOD FOR PRODUCING AN L-AMINO ACID USING A BACTERIUM OF THE FAMILY *ENTEROBACTERIACEAE* HAVING A DISRUPTED PUTRESCINE DEGRADATION PATHWAY

This application is a Continuation of, and claims priority under 35 U.S.C. §120 to, International Application No. PCT/JP2014/078157, filed Oct. 16, 2014, and claims priority therethrough under 35 U.S.C. §119 to Russian Patent Application No. 2013147882, filed Oct. 28, 2013, the entireties of which are incorporated by reference herein. Also, the Sequence Listing filed electronically herewith is hereby incorporated by reference (File name: 2016-04-13T_US-523_Seq_List; File size: 53 KB; Date recorded: Apr. 13, 2016).

BACKGROUND OF THE INVENTION

Technical Field

The present invention relates to the microbiological industry, and specifically to a method for producing L-amino acids by fermentation of a bacterium of the family Enterobacteriaceae that has been modified to disrupt putrescine degradation pathway.

Background Art

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acid production yields have been reported, including transformation of microorganisms with recombinant DNA (see, for example, U.S. Pat. No. 4,278,765 A) and alteration of regulatory regions such as promoter, leader sequence, and/or attenuator, or others known to the person skilled in the art (see, for example, US20060216796 A1 and WO9615246 A1). Other techniques for enhancing production yields include increasing the activities of enzymes involved in amino acid biosynthesis and/or desensitizing the target enzymes to the feedback inhibition by the resulting L-amino acid (see, for example, WO9516042 A1, EP0685555 A1 or U.S. Pat. Nos. 4,346,170 A, 5,661,012 A, and 6,040,160 A).

Another method for enhancing L-amino acids production yields is to attenuate expression of a gene or several genes which are involved in degradation of the target L-amino acid, genes which divert the precursors of the target L-amino acid from the L-amino acid biosynthetic pathway, genes involved in the redistribution of the carbon, nitrogen, and phosphate fluxes, and genes encoding toxins, etc.

The pathways that result in the production of arginine, ornithine, putrescine, and γ-aminobutyric acid (GABA) catabolism are related (Schneider B. L. et al., Arginine catabolism and the arginine succinyltransferase pathway in *Escherichia coli*, J. Bacteriol., 1998, 180(16):4278-4286). Arginine and ornithine are degraded via the ammonia-producing arginine succinyltransferase (AST) pathway to glutamate by AST enzymes encoded by the astCADBE operon genes. The AST pathway is necessary for arginine degradation during nitrogen-limited growth, and it contributes to the degradation of other amino acids. Alternatively, to the AST pathway, another arginine catabolic pathway via agmatine to putrescine exists, which utilizes arginine decarboxylase (ADC) in the initial reaction (ADC pathway). The ADC pathway is not used to degrade arginine when it is the sole nitrogen source (Schneider B. L. et al., Putrescine catabolism is a metabolic response to several stresses in *Escherichia coli*, Mol. Microbiol., 2013, 88(3):537-550). Contrary to the arginine degradation pathway, ornithine is directly converted to putrescine by ornithine decarboxylase (ODC) in the ODC pathway.

Putrescine, which can also be referred to as tetramethylenediamine or 1,4-diaminobutane, is degraded via GABA to succinate for use as a carbon and nitrogen source by either the glutamylated putrescine (GP) pathway or the transaminase pathway. The GP pathway, also referred to as Puu pathway, utilizes the enzymes to completely degrade putrescine to succinate. The puuA, puuB, puuC, puuD and puuE genes, along with puuP and puuR genes encoding a putrescine/H$^+$ symporter PuuP and DNA-binding transcriptional repressor PuuR, are organized in the puu divergon. The puu gene cluster was found in *Escherichia coli* (*E. coli*) and closely related enterobacteria (Nemoto N. et al., Mechanism for regulation of the putrescine utilization pathway by the transcription factor PuuR in *Escherichia coli* K-12, J. Bacteriol., 2012, 194(13):3437-3447). It is postulated that *E. coli* and related enterobacteria may utilize the GP pathway as an adaptation for survival in the mammalian intestine, an environment in which polyamines exist at relatively high concentrations. PatA, PatD, GabT, and GabD constitute the transaminase pathway of putrescine degradation (Schneider B. L. et al., 2013, 88(3):537-550).

Until now, no data has been reported demonstrating the effect of the disruption of putrescine degradation pathway on L-amino acid production by modified bacterial strains of the family Enterobacteriaceae.

SUMMARY OF THE INVENTION

An aspect of the present invention is to provide a bacterium belonging to the family Enterobacteriaceae, which can belong to the genus *Escherichia* and, more specifically, to the species *E. coli*, which has been modified to disrupt a putrescine degradation pathway such as, for example, the glutamylated putrescine pathway or the transaminase pathway.

Another aspect of the present invention is to provide a method for producing L-amino acids such as L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine using a bacterium of the family Enterobacteriaceae as described hereinafter.

These aims were achieved by the unexpected findings that disruption of a putrescine degradation pathway confers on the microorganism higher productivity of L-amino acids, in particular, but is not limited to the L-amino acids belonging to the glutamate family such as L-arginine and L-ornithine. For example, a putrescine degradation pathway such as the glutamylated putrescine pathway can be disrupted by deregulation of expression of at least one gene encoding an enzyme from the pathway, in particular, inactivation of one gene or several genes from the puuADRCBE gene cluster on the chromosome of a bacterium belonging to the family Enterobacteriaceae, which can belong to the genus *Escherichia* and, more specifically, to the species *E. coli*. These findings have resulted in the following non-limiting aspects of the present invention.

An aspect of the present invention is to provide a method for producing an L-amino acid comprising:

(i) cultivating an L-amino acid-producing bacterium of the family Enterobacteriaceae in a culture medium; and (ii) collecting said L-amino acid in the bacterium or culture medium, or both, wherein the bacterium has been modified to disrupt a putrescine degradation pathway.

It is a further aspect of the present invention to provide the method as described above, wherein the putrescine degradation pathway is a transaminase pathway or a glutamylated putrescine pathway.

It is a further aspect of the present invention to provide the method as described above, wherein the putrescine degradation pathway is disrupted by attenuation of expression of a gene selected from the group consisting of patA, patD, gabT, gabD, puuA, puuB, puuC, puuD, puuE, and combinations thereof.

It is a further aspect of the present invention to provide the method as described above, wherein the putrescine degradation pathway is the glutamylated putrescine pathway, wherein the glutamylated putrescine pathway is disrupted by attenuation of expression of one gene or several genes from the puuADRCBE gene cluster, with the proviso that the puuR gene cannot be the only gene that is attenuated.

It is a further aspect of the present invention to provide the method as described above, wherein the putrescine degradation pathway is disrupted by attenuation of expression of the puuA gene or the entire puuADRCBE gene cluster.

It is a further aspect of the present invention to provide the method as described above, wherein expression of the gene(s) is/are attenuated by inactivation of said gene(s).

It is a further aspect of the present invention to provide the method as described above, wherein the said gene(s) is/are deleted.

It is a further aspect of the present invention to provide the method as described above, wherein the bacterium belongs to the genus *Escherichia*.

It is a further aspect of the present invention to provide the method as described above, wherein the bacterium is *Escherichia coli*.

It is a further aspect of the present invention to provide the method as described above, wherein the bacterium belongs to the genus *Pantoea*.

It is a further aspect of the present invention to provide the method as described above, wherein the bacterium is *Pantoea ananatis*.

It is a further aspect of the present invention to provide the method as described above, wherein the L-amino acid is selected from the group consisting of L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine.

It is a further aspect of the present invention to provide the method as described above, wherein the L-amino acid belongs to the glutamate family and is selected from the group consisting of L-arginine, L-citrulline, L-glutamic acid, L-glutamine, L-ornithine, and L-proline.

It is a further aspect of the present invention to provide the method as described above, wherein the L-amino acid is L-arginine.

It is a further aspect of the present invention to provide the method as described above, wherein the L-amino acid is L-ornithine.

DESCRIPTION OF THE PREFERRED EMBODIMENTS

The present invention is described in detail below.

1. Bacterium

The phrase "an L-amino acid-producing bacterium" can mean a bacterium of the family Enterobacteriaceae that has an ability to produce, excrete or secrete, and/or cause accumulation of an L-amino acid in a culture medium or the bacterial cells when the bacterium is cultured in the medium.

The phrase "an L-amino acid-producing bacterium" can also mean a bacterium which is able to produce, excrete or secrete, and/or cause accumulation of an L-amino acid in a culture medium in an amount larger than a wild-type or parental strain, such as *E. coli* K-12, and can mean that the microorganism is able to cause accumulation in a medium of an amount not less than 0.5 g/L, or not less than 1.0 g/L, of the target L-amino acid. The bacterium can produce either one kind of amino acid solely, or a mixture of two or more kinds of amino acids.

The phrase "L-amino acid-producing ability" can mean the ability of the bacterium to produce, excrete or secrete, and/or cause accumulation of the L-amino acid in a medium or the bacterial cells to such a level that the L-amino acid can be collected from the medium or the bacterial cells, when the bacterium is cultured in the medium.

The phrase "L-amino acid" can mean L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine.

The phrase "aromatic L-amino acid" can include, for example, L-phenylalanine, L-tryptophan, and L-tyrosine. As L-histidine has an aromatic moiety, specifically, an imidazole ring, the phrase "aromatic L-amino acid" can also include, besides the aforementioned aromatic L-amino acids, L-histidine.

The phrase "non-aromatic L-amino acid" can include, for example, L-alanine, L-arginine, L-asparagine, L-aspartic acid, L-citrulline, L-cysteine, L-glutamic acid, L-glutamine, glycine, L-isoleucine, L-leucine, L-lysine, L-methionine, L-ornithine, L-proline, L-serine, L-threonine, and L-valine. As the biosynthetic pathway of aromatic amino acids such as L-phenylalanine, L-tryptophan, and L-tyrosine is different from the biosynthetic pathway of L-histidine, the phrase "non-aromatic L-amino acid" can also include, besides the aforementioned non-aromatic L-amino acids, L-histidine.

An L-amino acid can belong to more than one L-amino acid family. As an example, L-amino acids belonging to the glutamate family include L-arginine, L-glutamic acid, L-glutamine, and L-proline; L-amino acids belonging to the serine family include L-cysteine, glycine, and L-serine; L-amino acids belonging to the aspartate family include L-asparagine, L-aspartic acid, L-isoleucine, L-lysine, L-methionine, and L-threonine; L-amino acids belonging to the pyruvate family include L-alanine, L-isoleucine, L-valine, and L-leucine; and L-amino acids belonging to the aromatic family include L-phenylalanine, L-tryptophan, and L-tyrosine. As some L-amino acids can be an intermediate in the biosynthetic pathway of another L-amino acid, the aforementioned families of amino acids may also include other L-amino acids, for example, non-proteinogenic L-amino acids. For example, L-citrulline and L-ornithine are amino acids from the arginine biosynthetic pathway. Therefore, the glutamate family may include L-arginine, L-citrulline, L-glutamic acid, L-glutamine, L-ornithine, and L-proline.

L-Arginine, L-cysteine, L-glutamic acid, L-histidine, L-isoleucine, L-lysine, L-ornithine, L-phenylalanine, L-proline, L-threonine, L-tryptophan, and L-valine are particular examples. The glutamate family amino acids such as L-arginine, L-citrulline, L-glutamic acid, L-glutamine, L-ornithine, and L-proline are specific examples. L-Arginine and L-ornithine are particular examples.

The phrase "L-amino acid" can mean not only an L-amino acid in a free form, but may also mean a salt or a hydrate of the L-amino acid, or an adduct formed by the L-amino acid and another organic or inorganic compound as described hereinafter. Salts of amino acids include sulfates, hydrochlorides, carbonates, ammonium salts, sodium salts, and potassium salts.

The bacteria belonging to the family Enterobacteriaceae can be from the genera *Escherichia* and/or *Pantoea*, and so forth, and can have the ability to produce an L-amino acid. Specifically, those classified into the family Enterobacteriaceae according to the taxonomy used in the NCBI (National Center for Biotechnology Information) database (ncbi.nlm.nih.gov/Taxonomy/Browser/wwwtax.cgi?id=543) can be used. Examples of strains from the family Enterobacteriaceae that can be modified include a bacterium of the genus *Escherichia, Enterobacter* or *Pantoea*.

Strains of *Escherichia* bacterium which can be modified to obtain *Escherichia* bacteria in accordance with the presently disclosed subject matter are not particularly limited, and specifically, those described in the work of Neidhardt et al. can be used (Bachmann, B. J., Derivations and genotypes of some mutant derivatives of *E. coli* K-12, p. 2460-2488. In F. C. Neidhardt et al. (ed.), *E. coli* and *Salmonella*: cellular and molecular biology, 2$^{nd}$ ed. ASM Press, Washington, D.C., 1996). The species *E. coli* is a particular example. Specific examples of *E. coli* include *E. coli* W3110 (ATCC 27325), *E. coli* MG1655 (ATCC 47076, ATCC 700926), and so forth, which are derived from the prototype wild-type strain, *E. coli* K-12 strain. These strains are available from, for example, the American Type Culture Collection (P.O. Box 1549, Manassas, Va. 20108, United States of America). That is, registration numbers are given to each of the strains, and the strains can be ordered by using these registration numbers (refer to atcc.org). The registration numbers of the strains are listed in the catalogue of the American Type Culture Collection.

Examples of the *Enterobacter* bacteria can include *Enterobacter agglomerans, Enterobacter aerogenes*, and so forth. Examples of the *Pantoea* bacteria can include *Pantoea ananatis*, and so forth. Some strains of *Enterobacter agglomerans* were recently reclassified into *Pantoea agglomerans, Pantoea ananatis* or *Pantoea stewartii* on the basis of nucleotide sequence analysis of 16S rRNA, etc. A bacterium belonging to any of the genus *Enterobacter* or *Pantoea* may be used so long as it is a bacterium classified into the family Enterobacteriaceae. When a *Pantoea ananatis* strain is bred by genetic engineering techniques, *Pantoea ananatis* AJ13355 strain (FERM BP-6614), AJ13356 strain (FERM BP-6615), AJ13601 strain (FERM BP-7207) and derivatives thereof can be used. These strains were identified as *Enterobacter agglomerans* when they were isolated, and deposited as *Enterobacter agglomerans*. However, they were recently re-classified as *Pantoea ananatis* on the basis of nucleotide sequencing of 16S rRNA and so forth as described above.

L-Amino Acid-Producing Bacteria

A bacterium belonging to the family Enterobacteriaceae and modified to disrupt putrescine degradation pathway, which is able to produce an L-amino acid, can be used.

The bacterium may inherently have the L-amino acid-producing ability or may be modified to have an L-amino acid-producing ability by using a mutation method or DNA recombination techniques. The bacterium can be modified to contain the disrupted putrescine degradation pathway in a bacterium which inherently has the ability to produce an L-amino acid. Alternatively, the bacterium can be obtained by imparting the ability to produce an L-amino acid to a bacterium already modified to disrupt putrescine degradation pathway.

L-Arginine-Producing Bacteria

Examples of parental strains which can be used to derive L-arginine-producing bacteria include, but are not limited to, strains belonging to the genus *Escherichia* such as *E. coli* strain 237 (VKPM B-7925) (U.S. Patent Application 2002/058315 A1) and its derivative strains harboring mutant N-acetylglutamate synthase (Russian Patent No. 2215783), *E. coli* strain 382 (VKPM B-7926, EP1170358 A1), an L-arginine-producing strain into which argA gene encoding N-acetylglutamate synthetase is introduced therein (EP1170361 A1), and the like.

Examples of parental strains that can be used to derive L-arginine-producing bacteria can also include strains in which expression of one or more genes encoding an L-arginine biosynthetic enzyme are enhanced. Examples of such genes include genes encoding N-acetyl-γ-glutamylphosphate reductase (argC), ornithine acetyltransferase (argJ), N-acetylglutamate kinase (argB), N-acetylornithine aminotransferase (argD), ornithine carbamoyltransferase (argF), argininosuccinate synthase (argG), argininosuccinate lyase (argH), and carbamoyl phosphate synthetase (carAB).

L-Citrulline-Producing Bacteria

Examples of parental strains that can be used to derive L-citrulline-producing bacteria can include, but are not limited to, strains belonging to the genus *Escherichia* such as *E. coli* mutant N-acetylglutamate synthase strains 237/pMADS11, 237/pMADS12, and 237/pMADS13 (Russian Patent No. 2215783, European Patent No. 1170361 B1, U.S. Pat. No. 6,790,647 B2). *E. coli* strains 333 (VKPM B-8084) and 374 (VKPM B-8086), both of which harbor harbor mutant feedback-resistant carbamoyl phosphate synthetase (Russian Patent RU2264459 C2), *E. coli* strains in which α-ketoglutarate synthase activity is increased, and ferredoxin NADP$^+$ reductase, pyruvate synthase or α-ketoglutarate dehydrogenase activities are additionally modified (EP 2133417 A1), and *P. ananantis* strain NA1sucAsdhA, in which succinate dehydrogenase and α-ketoglutarate dehydrogenase activities are decreased (US Patent Application No 2009286290), and the like, are further examples.

As L-citrulline is an intermediate of L-arginine biosynthetic pathway, examples of parent strains, which can be used to derive L-citrulline-producing bacteria, include strains, in which expression of one or more genes encoding an L-arginine biosynthetic enzyme is enhanced. Examples of such genes include, but are not limited to, genes encoding N-acetylglutamate synthase (argA), N-acetylglutamate kinase (argB), N-acetylglutamyl phosphate reductase (argC), acetylornithine transaminase (argD), acetylornithine deacetylase (argE), ornithine carbamoyltransferase (argF/I), and carbamoyl phosphate synthetase (carAB), and combinations thereof.

L-Citrulline-producing bacterium can be also easily obtained from any L-arginine-producing bacterium, for example *E. coli* 382 stain (VKPM B-7926), by inactivation of argininosuccinate synthase encoded by argG gene.

L-Cysteine-Producing Bacteria

Examples of parental strains which can be used to derive L-cysteine-producing bacteria can include, but are not limited to, strains belonging to the genus *Escherichia* such as *E. coli* JM15 which is transformed with different cysE alleles encoding feedback-resistant serine acetyltransferases (U.S. Pat. No. 6,218,168, Russian patent No. 2279477), *E. coli* W3110 having overexpressed genes which encode proteins suitable for secreting substances toxic for cells (U.S. Pat. No. 5,972,663), *E. coli* strains having lowered cysteine desulfohydrase activity (JP11155571 A2), *E. coli* W3110 with increased activity of a positive transcriptional regulator for cysteine regulon encoded by the cysB gene (WO0127307 A1), *E. coli* JM15(ydeD) (U.S. Pat. No. 6,218,168), and the like.

L-Glutamic Acid-Producing Bacteria

Examples of parental strains that can be used to derive L-glutamic acid-producing bacteria can include, but are not limited to, strains belonging to the genus *Escherichia* such as *E. coli* VL334thrC$^+$ (EP 1172433). The *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* strain K-12 (VKPM B-7) cells. As a result, an L-isoleucine auxotrophic strain VL334thrC$^+$ (VKPM B-8961), which is able to produce L-glutamic acid, was obtained.

Examples of parental strains, which can be used to derive the L-glutamic acid-producing bacteria can include, but are not limited to strains in which expression of one or more genes encoding an L-glutamic acid biosynthetic enzyme are enhanced. Examples of such genes include genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), and glucose phosphate isomerase (pgi).

Examples of strains modified so that expression of the citrate synthetase gene, the phosphoenolpyruvate carboxylase gene, and/or the glutamate dehydrogenase gene is/are enhanced include those disclosed in EP1078989 A2, EP955368 A2, and EP952221 A2.

Examples of parental strains, which can be used to derive the L-glutamic acid-producing bacteria, can also include strains having decreased or eliminated activity of an enzyme that catalyzes synthesis of a compound other than L-glutamic acid by branching off from an L-glutamic acid biosynthesis pathway. Examples of such enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), and glutamate decarboxylase (gadAB). Bacteria belonging to the genus *Escherichia* deficient in the α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

*E. coli* W3110sucA::Km$^R$
*E. coli* AJ12624 (FERM BP-3853)
*E. coli* AJ12628 (FERM BP-3854)
*E. coli* AJ12949 (FERM BP-4881)

*E. coli* W3110sucA::Km$^R$ is a strain obtained by disrupting the α-ketoglutarate dehydrogenase gene (hereinafter referred to as "sucA gene") of *E. coli* W3110. This strain is completely deficient in α-ketoglutarate dehydrogenase.

Other examples of L-glutamic acid-producing bacterium include those that belong to the genus *Escherichia* and have resistance to an aspartic acid antimetabolite. These strains can also be deficient in the α-ketoglutarate dehydrogenase activity and can include, for example, *E. coli* AJ13199 (FERM BP-5807) (U.S. Pat. No. 5,908,768), FFRM P-12379, which additionally has a low L-glutamic acid decomposing ability (U.S. Pat. No. 5,393,671), AJ13138 (FERM BP-5565) (U.S. Pat. No. 6,110,714), and the like.

Examples of L-glutamic acid-producing bacteria include mutant strains belonging to the genus *Pantoea* that are deficient in the α-ketoglutarate dehydrogenase activity or have a decreased α-ketoglutarate dehydrogenase activity, and can be obtained as described above. Such strains include *Pantoea ananatis* AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, Incorporated Administrative Agency, National Institute of Technology and Evaluation, International Patent Organism Depositary (NITE-IPOD), #120, 2-5-8 Kazusakamatari, Kisarazu-shi, Chiba-ken 292-0818, JAPAN) on Feb. 19, 1998 under an accession number of FERM P-16645. It was then converted to an international deposit under the provisions of Budapest Treaty on Jan. 11, 1999 and received an accession number of FERM BP-6615. *Pantoea ananatis* AJ13356 is deficient in α-ketoglutarate dehydrogenase activity as a result of disruption of the αKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

L-Histidine-Producing Bacteria

Examples of parental strains which can be used to derive L-histidine-producing bacteria can include but are not limited to strains belonging to the genus *Escherichia* such as *E. coli* strain 24 (VKPM B-5945, RU2003677), *E. coli* strain 80 (VKPM B-7270, RU2119536), *E. coli* NRRL B-12116-B12121 (U.S. Pat. No. 4,388,405), *E. coli* H-9342 (FERM BP-6675) and H-9343 (FERM BP-6676) (U.S. Pat. No. 6,344,347), *E. coli* H-9341 (FERM BP-6674) (EP1085087), *E. coli* AI80/pFM201 (U.S. Pat. No. 6,258,554), and the like.

Examples of parental strains that can be used to derive L-histidine-producing bacteria can also include strains in which expression of one or more genes encoding an L-histidine biosynthetic enzyme are enhanced. Examples of such genes include genes encoding ATP phosphoribosyltransferase (hisG), phosphoribosyl-AMP cyclohydrolase (hisI), phosphoribosyl-AMP cyclohydrolase/phosphoribosyl-ATP pyrophosphatase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore L-histidine-producing ability can also be efficiently enhanced by introducing a mutation into ATP phosphoribosyltransferase to confer resistance to feedback inhibition (Russian Patent Nos. 2003677 and 2119536).

Specific examples of strains having an L-histidine-producing ability include E. coli FERM-P 5038 and 5048 which have been transformed with a vector carrying a DNA encoding an L-histidine-biosynthetic enzyme (JP 56-005099 A), E. coli strains transformed with rht, a gene for an amino acid-export (EP1016710A), E. coli 80 strain imparted with sulfaguanidine, DL-1,2,4-triazole-3-alanine, and streptomycin-resistance (VKPM B-7270, RU2119536), and E. coli MG1655+hisGr hisL'_ΔpurR (RU2119536 and Doroshenko V. G. et al., The directed modification of Escherichia coli MG1655 to obtain histidine-producing mutants, Prikl. Biochim. Mikrobiol. (Russian), 2013, 49(2):149-154.), and so forth.

L-Isoleucine-Producing Bacteria

Examples of parental strains which can be used to derive L-isoleucine-producing bacteria include, but are not limited to mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parental strains (JP 2-458 A, EP0356739 A1, and U.S. Pat. No. 5,998,178).

L-Leucine-Producing Bacteria

Examples of parental strains which can be used to derive L-leucine-producing bacteria include, but are not limited to strains belonging to the genus Escherichia such as E. coli strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (JP 62-34397 B and JP 8-70879 A); E. coli strains obtained by the gene engineering method described in WO96/06926; E. coli H-9068 (JP 8-70879 A), and the like.

The bacterium can be improved by enhancing the expression of one or more genes involved in L-leucine biosynthesis. Examples include genes of the leuABCD operon, which can be represented by a mutant leuA gene encoding isopropylmalate synthase freed from feedback inhibition by L-leucine (U.S. Pat. No. 6,403,342). In addition, the bacterium can be improved by enhancing the expression of one or more genes encoding proteins that excrete L-amino acid from the bacterial cell. Examples of such genes include b2682 and b2683 (ygaZH genes) (EP1239041 A2).

L-Lysine-Producing Bacteria

Examples of L-lysine-producing bacteria belonging to the family Escherichia include mutants having resistance to an L-lysine analogue. The L-lysine analogue inhibits growth of bacteria belonging to the genus Escherichia, but this inhibition is fully or partially desensitized when L-lysine is present in the medium. Examples of the L-lysine analogue include, but are not limited to oxalysine, lysine hydroxamate, S-(2-aminoethyl)-L-cysteine (AEC), γ-methyllysine, α-chlorocaprolactam, and so forth. Mutants having resistance to these lysine analogues can be obtained by subjecting bacteria belonging to the genus Escherichia to a conventional artificial mutagenesis treatment. Specific examples of bacterial strains useful for producing L-lysine include E. coli AJ11442 (FERM BP-1543, NRRL B-12185; see U.S. Pat. No. 4,346,170) and E. coli VL611. In these microorganisms, feedback inhibition of aspartokinase by L-lysine is desensitized.

Examples of parental strains which can be used to derive L-lysine-producing bacteria also include, but are not limited to strains in which expression of one or more genes encoding an L-lysine biosynthetic enzyme are enhanced. Examples of such genes include, but are not limited to genes encoding dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenease (asd), and aspartase (aspA) (EP1253195 A1). In addition, the parental strains may have an increased level of expression of the gene involved in energy efficiency (cyo) (EP1170376 A1), the gene encoding nicotinamide nucleotide transhydrogenase (pntAB) (U.S. Pat. No. 5,830,716), the ybjE gene (WO2005/073390), or combinations thereof.

L-Amino acid-producing bacteria may have reduced or no activity of an enzyme that catalyzes a reaction which causes a branching off from the L-amino acid biosynthesis pathway and results in the production of another compound. Also, the bacteria may have reduced or no activity of an enzyme that negatively acts on L-amino acid synthesis or accumulation. Examples of such enzymes involved in L-lysine production include homoserine dehydrogenase, lysine decarboxylase (cadA, ldcC), malic enzyme, and so forth, and strains in which activities of these enzymes are decreased or deleted are disclosed in WO95/23864, WO96/17930, WO2005/010175, and so forth.

Expression of both the cadA and ldcC genes encoding lysine decarboxylase can be decreased in order to decrease or delete the lysine decarboxylase activity. Expression of the both genes can be decreased by, for example, the method described in WO2006/078039.

Examples of L-lysine-producing bacteria can include the E. coli WC196ΔcadAΔldcC/pCABD2 strain (WO2006/078039). The strain was constructed by introducing the plasmid pCABD2 containing lysine biosynthesis genes (U.S. Pat. No. 6,040,160) into the WC196 strain having disrupted cadA and ldcC genes which encode lysine decarboxylase.

The WC196 strain was bred from the W3110 strain, which was derived from E. coli K-12 by replacing the wild-type lysC gene on the chromosome of the W3110 strain with a mutant lysC gene encoding a mutant aspartokinase III in which threonine at position 352 was replaced with isoleucine, resulting in desensitization of the feedback inhibition by L-lysine (U.S. Pat. No. 5,661,012), and conferring AEC resistance to the resulting strain (U.S. Pat. No. 5,827,698). The WC196 strain was designated E. coli AJ13069, deposited at the National Institute of Bioscience and Human-Technology, Agency of Industrial Science and Technology (currently, Incorporated Administrative Agency, National Institute of Technology and Evaluation, International Patent Organism Depositary (NITE-IPOD), #120, 2-5-8 Kazusakamatari, Kisarazu-shi, Chiba-ken 292-0818, JAPAN) on Dec. 6, 1994, and assigned an accession number of FERM P-14690. Then, it was converted to an international deposit under the provisions of the Budapest Treaty on Sep. 29, 1995, and assigned an accession number of FERM BP-5252 (U.S. Pat. No. 5,827,698).

The WC196ΔcadAΔldcC strain itself is also an exemplary L-lysine-producing bacterium. The WC196ΔcadAΔldcC was designated AJ110692 and deposited at the National Institute of Bioscience and Human-Technology, Agency of Industrial Science and Technology (currently, Incorporated Administrative Agency, National Institute of Technology and Evaluation, International Patent Organism Depositary (NITE-IPOD), #120, 2-5-8 Kazusakamatari, Kisarazu-shi, Chiba-ken 292-0818, JAPAN) on Oct. 7, 2008 as an international deposit under an accession number of FERM BP-11027.

L-Methionine-Producing Bacteria

Examples of L-methionine-producing bacteria and parent strains which can be used to derive L-methionine-producing bacteria include, but are not limited to *Escherichia* bacteria strains such as strains AJ11539 (NRRL B-12399), AJ11540 (NRRL B-12400), AJ11541 (NRRL B-12401), AJ 11542 (NRRL B-12402) (patent GB2075055); strains 218 (VKPM B-8125) (patent RU2209248) and 73 (VKPM B-8126) (patent RU2215782) resistant to norleucine, the L-methionine analog, or the like. The strain *E. coli* 73 has been deposited in the Russian National Collection of Industrial Microorganisms (VKPM) (Russian Federation, 117545 Moscow, 1$^{st}$ Dorozhny Proezd, 1) on May 14, 2001 under accession number VKPM B-8126, and was converted to an international deposit under the Budapest Treaty on Feb. 1, 2002. Furthermore, a methionine repressor-deficient strain and recombinant strains transformed with genes encoding proteins involved in L-methionine biosynthesis such as homoserine transsuccinylase and cystathionine γ-synthase (JP 2000-139471 A) can also be used as parent strains.

L-Ornithine-Producing Bacteria

L-ornithine-producing bacterium can be easily obtained from any L-arginine-producing bacterium, for example *E. coli* 382 stain (VKPM B-7926), by inactivation of ornithine carbamoyltransferase encoded by both argF and argI genes. Methods for inactivation of ornithine carbamoyltransferase are described herein.

L-Phenylalanine-Producing Bacteria

Examples of parental strains which can be used to derive L-phenylalanine-producing bacteria include, but are not limited to strains belonging to the genus *Escherichia* such as *E. coli* AJ12739 (tyrA::Tn10, tyrR) (VKPM B-8197), *E. coli* HW1089 (ATCC 55371) harboring the mutant pheA34 gene (U.S. Pat. No. 5,354,672), *E. coli* MWEC101-b (KR8903681), *E. coli* NRRL B-12141, NRRL B-12145, NRRL B-12146 and NRRL B-12147 (U.S. Pat. No. 4,407,952). Also, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662), and *E. coli* K-12 [W3110 (tyrA)/pBR-aroG4, pACMAB] named as AJ 12604 (FERM BP-3579) may be used as a parental strain (EP488424 B1). Furthermore, L-phenylalanine-producing bacteria belonging to the genus *Escherichia* with an enhanced activity of the protein encoded by the yedA gene or the yddG gene may also be used (U.S. patent applications 2003/0148473 A1 and 2003/0157667 A1).

L-Proline-Producing Bacteria

Examples of parental strains that can be used to derive L-proline-producing bacteria can include, but are not limited to strains belonging to the genus *Escherichia* such as *E. coli* 702ilvA (VKPM B-8012), which is deficient in the ilvA gene and is able to produce L-proline (EP1172433 A1). The bacterium can be improved by enhancing the expression of one or more genes involved in L-proline biosynthesis. Examples of genes that can be used in L-proline-producing bacteria include the proB gene encoding glutamate kinase with desensitized feedback inhibition by L-proline (DE3127361 A1). In addition, the bacterium can be improved by enhancing the expression of one or more genes encoding proteins responsible for excreting L-amino acids from the bacterial cell. Such genes can be exemplified by b2682 and b2683 (ygaZH genes) (EP1239041 A2).

Examples of bacteria belonging to the genus *Escherichia*, which have an activity to produce L-proline include the following *E. coli* strains: NRRL B-12403 and NRRL B-12404 (GB Patent 2075056), VKPM B-8012 (Russian Patent application No. 2000124295), plasmid mutants described in DE3127361 A1, plasmid mutants described by Bloom F. R. et al. in "The 15$^{th}$ Miami winter symposium", 1983, p. 34, and the like.

L-Threonine-Producing Bacteria

Examples of parental strains which can be used to derive L-threonine-producing bacteria include, but are not limited to strains belonging to the genus *Escherichia* such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., *Genetika* (*Russian*), 1978, 14:947-956), *E. coli* VL643 and VL2055 (EP1149911 A2), and the like.

The strain TDH-6 is deficient in the thrC gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain B-3996 was deposited on Nov. 19, 1987 in the All-Union Scientific Center of Antibiotics (Russian Federation, 117105 Moscow, Nagatinskaya Street 3-A) under the accession number RIA 1867. The strain was also deposited in the Russian National Collection of Industrial Microorganisms (VKPM) (Russian Federation, 117545 Moscow, 1$^{st}$ Dorozhny proezd, 1) on Apr. 7, 1987 under the accession number B-3996.

*E. coli* VKPM B-5318 (EP0593792 A1) may also be used as a parental strain for deriving L-threonine-producing bacteria. The strain B-5318 is prototrophic with regard to isoleucine; and a temperature-sensitive lambda-phage C1 repressor and PR promoter replace the regulatory region of the threonine operon in plasmid pVIC40. The strain VKPM B-5318 was deposited in the Russian National Collection of Industrial Microorganisms (VKPM) on May 3, 1990 under the accession number of VKPM B-5318.

The bacterium can be additionally modified to enhance expression of one or more of the following genes:

the mutant thrA gene which encodes aspartokinase homoserine dehydrogenase I resistant to feedback inhibition by threonine;

the thrB gene which encodes homoserine kinase;

the thrC gene which encodes threonine synthase;

the rhtA gene which encodes a putative transmembrane protein of the threonine and homoserine efflux system;

the asd gene which encodes aspartate-β-semialdehyde dehydrogenase; and the aspC gene which encodes aspartate aminotransferase (aspartate transaminase);

The thrA gene which encodes aspartokinase I and homoserine dehydrogenase I of *E. coli* has been elucidated (KEGG entry No. b0002; GenBank accession No. NC_000913.2; nucleotide positions: 337 to 2,799; Gene ID: 945803). The thrA gene is located between the thrL and thrB genes on the chromosome of *E. coli* K-12.

The thrB gene which encodes homoserine kinase of *E. coli* has been elucidated (KEGG entry No. b0003; GenBank accession No. NC_000913.2; nucleotide positions: 2,801 to 3,733; Gene ID: 947498). The thrB gene is located between the thrA and thrC genes on the chromosome of *E. coli* K-12.

The thrC gene which encodes threonine synthase of *E. coli* has been elucidated (KEGG entry No. b0004; GenBank accession No. NC_000913.2; nucleotide positions: 3,734 to 5,020; Gene ID: 945198). The thrC gene is located between the thrB and yaaX genes on the chromosome of *E. coli* K-12. All three genes function as a single threonine operon thrABC. To enhance expression of the threonine operon, the attenuator region which affects transcription is desirably removed from the operon (WO2005049808 A1, WO2003097839 A1).

The mutant thrA gene which encodes aspartokinase I and homoserine dehydrogenase I resistant to feedback inhibition by L-threonine, as well as, the thrB and thrC genes can be obtained as one operon from the well-known plasmid pVIC40 which is present in the L-threonine-producing *E. coli* strain VKPM B-3996. Plasmid pVIC40 is described in detail in U.S. Pat. No. 5,705,371.

The rhtA gene which encodes a protein of the threonine and homoserine efflux system (an inner membrane transporter) of *E. coli* has been elucidated (KEGG entry No. b0813; GenBank accession No. NC_000913.2; nucleotide positions: 848,433 to 849,320, complement; Gene ID: 947045). The rhtA gene is located between the dps and ompX genes on the chromosome of *E. coli* K-12 close to the glnHPQ operon, which encodes components of the glutamine transport system. The rhtA gene is identical to the ybiF gene (KEGG entry No. B0813).

The asd gene which encodes aspartate-β-semialdehyde dehydrogenase of *E. coli* has been elucidated (KEGG entry No. b3433; GenBank accession No. NC_000913.2; nucleotide positions: 3,571,798 to 3,572,901, complement; Gene ID: 947939). The asd gene is located between the glgB and gntU gene on the same strand (yhgN gene on the opposite strand) on the chromosome of *E. coli* K-12.

Also, the aspC gene which encodes aspartate aminotransferase of *E. coli* has been elucidated (KEGG entry No. b0928; GenBank accession No. NC_000913.2; nucleotide positions: 983,742 to 984,932, complement; Gene ID: 945553). The aspC gene is located between the ycbL gene on the opposite strand and the ompF gene on the same strand on the chromosome of *E. coli* K-12.

L-Tryptophan-Producing Bacteria

Examples of parental strains which can be used to derive the L-tryptophan-producing bacteria include, but are not limited to strains belonging to the genus *Escherichia* such as *E. coli* JP4735/pMU3028 (DSM10122) and JP6015/pMU91 (DSM10123) deficient in the tryptophanyl-tRNA synthetase encoded by mutant trpS gene (U.S. Pat. No. 5,756,345), *E. coli* SV164 (pGH5) having a serA allele encoding phosphoglycerate dehydrogenase free from feedback inhibition by serine and a trpE allele encoding anthranilate synthase free from feedback inhibition by tryptophan (U.S. Pat. No. 6,180,373), *E. coli* AGX17 (pGX44) (NRRL B-12263) and AGX6(pGX50)aroP (NRRL B-12264) deficient in the enzyme tryptophanase (U.S. Pat. No. 4,371,614), *E. coli* AGX17/pGX50, pACKG4-pps in which a phosphoenolpyruvate-producing ability is enhanced (WO9708333, U.S. Pat. No. 6,319,696), and the like may be used. L-tryptophan-producing bacteria belonging to the genus *Escherichia* with an enhanced activity of the identified protein encoded by and the yedA gene or the yddG gene may also be used (U.S. patent applications 2003/0148473 A1 and 2003/0157667 A1).

Examples of parental strains which can be used to derive the L-tryptophan-producing bacteria can also include strains in which one or more activities of the enzymes selected from anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, so that a mutation desensitizing the feedback inhibition may be introduced into these enzymes. Specific examples of strains having such a mutation include an *E. coli* SV164 which harbors desensitized anthranilate synthase and a transformant strain obtained by introducing into the *E. coli* SV164 the plasmid pGH5 (WO 94/08031), which contains a mutant serA gene encoding feedback-desensitized phosphoglycerate dehydrogenase.

Examples of parental strains which can be used to derive the L-tryptophan-producing bacteria can also include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of α and β subunits which are encoded by the trpA and trpB genes, respectively. In addition, L-tryptophan-producing ability may be improved by enhancing expression of the isocitrate lyase-malate synthase operon (WO2005/103275).

L-Valine-Producing Bacteria

Examples of parental strains which can be used to derive L-valine-producing bacteria can include, but are not limited to strains which have been modified to overexpress the ilvGMEDA operon (U.S. Pat. No. 5,998,178). It is desirable to remove the region of the ilvGMEDA operon which is required for attenuation so that expression of the operon is not attenuated by the L-valine that is produced. Furthermore, the ilvA gene in the operon is desirably disrupted so that threonine deaminase activity is decreased.

Examples of parental strains that can be used to derive L-valine-producing bacteria can also include mutants having a mutation of aminoacyl-tRNA synthetase (U.S. Pat. No. 5,658,766). For example, *E. coli* VL1970, which has a mutation in the ileS gene encoding isoleucine tRNA synthetase, can be used. *E. coli* VL1970 was deposited in the Russian National Collection of Industrial Microorganisms (VKPM) (Russian Federation, 117545 Moscow, 1$^{st}$ Dorozhny Proezd, 1) on Jun. 24, 1988 under the accession number VKPM B-4411.

Furthermore, mutants requiring lipoic acid for growth and/or lacking H$^{+}$-ATPase can also be used as parental strains (WO96/06926).

Examples of L-valine-producing strain include *E. coli* strain H-81 (VKPM B-8066), NRRL B-12287 and NRRL B-12288 (U.S. Pat. No. 4,391,907), VKPM B-4411 (U.S. Pat. No. 5,658,766), VKPM B-7707 (European patent application EP1016710A2), or the like.

The bacterium of the present invention belonging to the family Enterobacteriaceae can be modified to disrupt a putrescine degradation pathway, which can be either the transaminase pathway or glutamylated putrescine pathway.

Exemplary and without limiting the scope of the present invention, a putrescine degradation pathway can be disrupted by attenuation of expression of at least one gene encoding an enzyme from the pathway, in particular, inactivation of one gene or several genes from the puuADRCBE gene cluster, and/or one gene or several genes such as the patA, patD, gabT, or gabD genes on the chromosome of a bacterium belonging to the family Enterobacteriaceae such as a bacterium of the species *E. coli*.

The phrase "a putrescine degradation pathway" refers to one of the following pathways for degradation of putrescine such as "the transaminase pathway" or "the glutamylated putrescine pathway", which degrade putrescine to succinate via γ-aminobutyric acid (GABA) as explained hereinafter.

The phrase "the transaminase pathway" for degradation of putrescine refers to a set of consecutive enzymatic reactions catalyzed by putrescine transaminase (PatA), γ-aminobutyraldehyde dehydrogenase (PatD), γ-aminobutyrate transaminase (GabT), and succinic semialdehyde dehydrogenase (GabD), in which putrescine is converted into succinic acid (succinate) via γ-aminobutyraldehyde (ABAL), GABA and succinic semialdehyde (SSA) as described in Schneider B. L. et al., 2013, 88(3):537-550. The genes encoding enzymes from the transaminase pathway of *E. coli* have been elucidated such as patA (synonyms oat, pat, ygjG; KEGG, Kyoto Encyclopedia of Genes and Genomes, entry No. b3073; encodes PatA), patD (synonyms prr, ydcW; KEGG, entry No. b1444; encodes PatD), gabT (KEGG, entry No. b2662; encodes GabT), and gabD (KEGG, entry No. b2661; encodes GabD).

The phrase "the glutamylated putrescine pathway" for degradation of putrescine refers to a set of consecutive enzymatic reactions catalyzed by γ-glutamylputrescine synthase (PuuA), γ-glutamylputrescine oxidase (PuuB), γ-glutamyl-γ-aminobutyraldehyde dehydrogenase (PuuC), γ-glutamyl-γ-aminobutyrate hydrolase (PuuD), 4-aminobutyrate aminotransferase (PuuE), in which putrescine is converted into succinic acid (succinate) via γ-glutamyl putrescine, γ-glutamyl ABAL, γ-glutamyl GABA, GABA and SSA as described in Schneider B. L. et al., 2013, 88(3):537-550. The putrescine-binding repressor PuuR represses the glutamylated putrescine pathway. Therefore, attenuation of expression of the puuR gene alone may result in enhancing putrescine degradation pathway. Thus, attenuation of the puuR gene alone is not encompassed in disruption of the putrescine degradation pathway.

The genes encoding enzymes from the glutamylated putrescine pathway of *E. coli* have been elucidated such as puuA, puuB, puuC, puuD, puuE and puuR as described hereinafter. These genes are organized into the puuADRCBE gene cluster on the chromosome of *E. coli* strain K-12.

The puuA gene (synonym ycjK) encodes γ-glutamylputrescine synthase PuuA (KEGG, entry No. b1297; Protein Knowledgebase, UniProtKB/Swiss-Prot, accession No. P78061). The puuA gene (GenBank accession No. NC_000913.2; nucleotide positions: 1357514 to 1358932, complement; Gene ID: 946202) is located between the puuP gene on the same strand and the puuD gene on the opposite strand on the chromosome of *E. coli* strain K-12. The nucleotide sequence of the puuA gene and the amino acid sequence of the PuuA protein encoded by the puuA gene are shown in SEQ ID NO: 1 and SEQ ID NO: 2, respectively.

The puuD gene (synonym ycjL) encodes γ-glutamyl-γ-aminobutyrate hydrolase PuuD (KEGG, entry No. b1298; Protein Knowledgebase, UniProtKB/Swiss-Prot, accession No. P76038). The puuD gene (GenBank accession No. NC_000913.2; nucleotide positions: 1359144 to 1359908, complement; Gene ID: 945882) is located between the puuR gene on the same strand and the pupP gene on the opposite strand on the chromosome of *E. coli* strain K-12. The nucleotide sequence of the puuD gene and the amino acid sequence of the PuuD protein encoded by the puuD gene are shown in SEQ ID NO: 3 and SEQ ID NO: 4, respectively.

The puuR gene (synonym ycjC) encodes the DNA-binding transcriptional repressor for the puu divergon PuuR (KEGG, entry No. b1299; Protein Knowledgebase, UniProtKB/Swiss-Prot, accession No. P0A9U6). The puuD gene (GenBank accession No. NC_000913.2; nucleotide positions: 1359935 to 1360492, complement; Gene ID: 945886) is located between the puuD and puuC genes on the same strand on the chromosome of *E. coli* strain K-12. The nucleotide sequence of the puuR gene and the amino acid sequence of the PuuR protein encoded by the puuR gene are shown in SEQ ID NO: 5 and SEQ ID NO: 6, respectively.

The puuC gene (synonym aldH) encodes γ-glutamyl-γ-aminobutyraldehyde dehydrogenase PuuC (KEGG, entry No. b1300; Protein Knowledgebase, UniProtKB/Swiss-Prot, accession No. P23883). The puuC gene (GenBank accession No. NC_000913.2; nucleotide positions: 1360767 to 1362254, complement; Gene ID: 947003) is located between the puuR and puuB genes on the same strand on the chromosome of *E. coli* strain K-12. The nucleotide sequence of the puuC gene and the amino acid sequence of the PuuC protein encoded by the puuC gene are shown in SEQ ID NO: 7 and SEQ ID NO: 8, respectively.

The puuB gene (synonyms ycjA, ordL) encodes γ-glutamylputrescine oxidase PuuB (KEGG, entry No. b1301; Protein Knowledgebase, UniProtKB/Swiss-Prot, accession No. P37906). The puuB gene (GenBank accession No. NC_000913.2; nucleotide positions: 1362256 to 1363536, complement; Gene ID: 945072) is located between the puuC and puuB genes on the same strand on the chromosome of *E. coli* strain K-12. The nucleotide sequence of the puuB gene and the amino acid sequence of the PuuB protein encoded by the puuB gene are shown in SEQ ID NO: 9 and SEQ ID NO: 10, respectively.

The puuE gene (synonym goaG) encodes the 4-aminobutyrate aminotransferase PuuE (KEGG, entry No. b1302; Protein Knowledgebase, UniProtKB/Swiss-Prot, accession No. P50457). The puuB gene (GenBank accession No. NC_000913.2; nucleotide positions: 1363574 to 1364839, complement; Gene ID: 945446) is located between the puuB on the same strand and the pspF gene on the opposite strand on the chromosome of *E. coli* strain K-12. The nucleotide sequence of the puuE gene and the amino acid sequence of the PuuE protein encoded by the puuE gene are shown in SEQ ID NO: 11 and SEQ ID NO: 12, respectively.

A "pathway," which can be also referred to as "a biochemical pathway" or "a metabolic pathway," can mean a set of anabolic or catabolic (bio)chemical reactions which act collectively to convert one biomolecule species into another one. Thus, the "pathway" can include a series of (bio)chemical reactions connected by their intermediates, that is, one or more products of one reaction is/are the substrate(s) for subsequent one or more reactions, and so forth. The meaning of the phrase "pathway" is usually apparent to the person skilled in the art.

The phrase "a bacterium modified to disrupt a putrescine degradation pathway" can mean that the bacterium has been modified in such a way that in the modified bacterium the carbon flux through one or more (bio)chemical reactions of the pathway is lower or even absent as compared with a bacterium in which the putrescine degradation pathway is not disrupted such as in a non-modified bacterium, for example, a wild-type or parental strain such as E. coli K-12. In the bacterium, which has been modified to disrupt the putrescine degradation pathway, the carbon flux through one or more (bio)chemical reactions of the pathway can be 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 0%, as compared with the carbon flux in the pathway of a non-modified bacterium.

The phrase "carbon flux" can mean the rate of turnover of carbon-containing molecules through a metabolic pathway. For example, the carbon flux of an amino acid such as, for example, L-arginine or L-ornithine can be calculated to determine carbon distribution from the L-amino acid in a putrescine degradation pathway such as the transaminase pathway or glutamylated putrescine pathway (Szyperski T. Biosynthetically directed fractional $^{13}$C-labeling of proteinogenic amino acids. An efficient analytical tool to investigate intermediary metabolism, *Eur. J. Biochem.,* 1995, 232: 433-448; Stephanopoulos, G., Aristidou, A. A., Nielsen, J. Metabolic engineering: principles and methodologies, Academic Press, $1^{st}$ ed., (1998); Matsuoka Y. and Shimizu K. $^{13}$C-Metabolic flux analysis and metabolic regulation, Chemical Biology, Prof. Deniz Ekinci (Ed.), DOI: 10.5772/35121, intechopen.com/books/chemical-biology/13c-metabolic-flux-analysis-and-metabolic-regulation).

The phrase "a bacterium modified to disrupt putrescine degradation pathway" can also mean that the bacterium has been modified in such a way that in the modified bacterium, the putrescine degradation pathway is attenuated.

The phrase "in the modified bacterium, the putrescine degradation pathway is attenuated" can mean that the bacterium has been modified in such a way that in the modified bacterium the expression of at least one gene encoding an enzyme from the putrescine degradation pathway is attenuated. For example, expression of one gene or several genes selected from patA, patD, gabT and gabD, encoding enzymes from the transaminase pathway, can be attenuated. In another example, expression of one or several of the puuA, puuB, puuC, puuD, puuE and puuR genes, encoding enzymes from the glutamylated putrescine pathway, can be attenuated. In yet another example, expression of one or several of the patA, patD, gabT, gabD, puuA, puuB, puuC, puuD, puuE and puuR genes may be attenuated. A combination of genes, expression of which can be attenuated to disrupt the putrescine degradation pathway, is not specifically limited so long as the attenuation of one gene or several genes results in disruption of the pathway. That is, expression of one or several of the patA, patD, gabT, gabD, puuA, puuB, puuC, puuD, and puuE genes can be attenuated in any combination to disrupt the putrescine degradation pathway so long as the bacterium has L-amino acid-producing ability. For example, expression of one gene such as, for example, puuA can be attenuated, or all of the puuA, puuB, puuC, puuD, puuE and puuR genes, constituting the entire puuADRCBE gene cluster, can be attenuated to disrupt the putrescine degradation pathway. However, attenuation of the puuR gene is not essential for disruption of the putrescine degradation pathway.

The phrase "several genes" can mean two or more genes such as, for example, three, four, five, six, seven, eight, nine or ten genes, or more. Therefore, the phrase "one or several genes" can mean a single gene such as, for example, the puuA gene, or an operon such as, for example, the puuCBE operon, or even an entire gene cluster such as, for example, the puuADRCBE gene cluster as described herein. It is, therefore, acceptable that the phrases "one or several genes" and "at least one gene" are equivalent.

For the purposes of the present invention, explanations given hereinafter as to proteins and genes encoding thereof from the glutamylated putrescine pathway can be applied mutatis mutandis to proteins and genes encoding thereof from the transaminase pathway. Furthermore, for the purposes of the present invention, explanations given hereinafter as to the puuADRCBE gene cluster can be applied mutatis mutandis to one or several of the patA, patD, gabT, gabD, puuA, puuB, puuC, puuD, and puuE genes, or a combination thereof.

The phrase "a bacterium modified to attenuate expression of at least one gene from the puuADRCBE gene cluster" can mean that the bacterium has been modified in such a way that in the modified bacterium, the expression of at least one gene from the puuADRCBE gene cluster is decreased as compared to a bacterium which contains a non-modified puuADRCBE gene cluster, for example, a wild-type or parental strain.

The phrase "attenuation" or "attenuated" can mean the alteration or modification of at least one gene in a bacterium that encodes an enzyme from the putrescine degradation pathway, such that an amount or activity of one or more enzymes in the bacterium is decreased or absent, thereby decreasing or completely eliminating the activity of the gene products.

The phrase "at least one gene from the puuADRCBE gene cluster gene is inactivated" can mean that at least one of the genes such as puuA, puuB, puuC, puuD, puuE and puuR from the modified gene cluster encodes a completely inactive or non-functional protein, as compared with a bacterium which contains the non-modified gene or non-modified puuADRCBE gene cluster.

It is also possible that at least one of the modified DNA regions from the puuADRCBE gene cluster is unable to naturally express the gene due to deletion of a part of the gene or deletion of the entire gene, replacement of one base or more to cause an amino acid substitution in the protein encoded by the gene (missense mutation), introduction of a stop codon (nonsense mutation), deletion of one or two bases to cause a reading frame shift of the gene, insertion of a drug-resistance gene and/or transcription termination signal, or modification of an adjacent region of the gene, including sequences controlling gene expression such as promoter(s), enhancer(s), attenuator(s), ribosome-binding site(s) (RBS), etc. Inactivation of at least one gene from the puuADRCBE gene cluster can also be performed, for example, by conventional methods such as a mutagenesis treatment using UV irradiation or nitrosoguanidine (N-methyl-N'-nitro-N-nitrosoguanidine), site-directed mutagenesis, gene disruption using homologous recombination, and/or insertion-deletion mutagenesis (Yu D. et al., *Proc. Natl. Acad. Sci. USA,* 2000, 97(11):5978-5983; Datsenko K. A. and Wanner B. L., *Proc. Natl. Acad. Sci. USA,* 2000, 97(12):6640-6645; Zhang Y. et al., *Nature Genet.,* 1998, 20:123-128) based on "Red/ET-driven integration" or "λRed/ET-mediated integration".

The phrase "the expression of at least one gene from the puuADRCBE gene cluster is attenuated" can mean that an amount of the protein(s) encoded by modified gene(s) from the puuADRCBE gene cluster such as puuA, puuB, puuC, puuD, puuE and puuR in the modified bacterium, in which expression of the gene(s) is/are attenuated, is/and educed as compared with a non-modified bacterium, for example, a wild-type or parental strain such as E. coli K-12.

The phrase "at least one gene from the puuADRCBE gene cluster is attenuated" can also mean that the modified bacterium contains one or more regions operably linked to one or more genes from the puuADRCBE gene cluster, including sequences controlling expression of genes from the puuADRCBE gene cluster such as promoters, enhancers, attenuators and transcription termination signals, ribosome-binding sites (RBS), and other expression control elements, which are modified resulting in a decrease in the expression level of at least one gene from the puuADRCBE gene cluster; and other examples (see, for example, WO95/34672; Carrier T. A. and Keasling J. D., *Biotechnol. Prog.*, 1999, 15:58-64). The phrase "operably linked to the gene" is a specific example of the phrase "operably linked to one or more genes," and can mean that the regulatory region(s) is/are linked to the nucleotide sequence of the nucleic acid molecule or gene in a manner which allows for expression (e.g., enhanced, increased, constitutive, basal, antiterminated, attenuated, deregulated, decreased or repressed expression) of the nucleotide sequence, specifically, expression of a gene product encoded by the nucleotide sequence.

Expression of at least one gene from the puuADRCBE gene cluster can be attenuated by replacing an expression control sequence of the gene, such as a promoter on the chromosomal DNA, with a weaker one. The strength of a promoter is defined by the frequency of initiation acts of RNA synthesis. Examples of methods for evaluating the strength of promoters and strong promoters are described in Goldstein M. A. et al. (Goldstein M. A. and Doi R. H., Prokaryotic promoters in biotechnology, *Biotechnol. Annu. Rev.*, 1995, 1:105-128), and so forth. Furthermore, it is also possible to introduce a nucleotide substitution for several nucleotides in a promoter region of a target gene and thereby modify the promoter to be weakened as disclosed in International Patent Publication WO00/18935. Furthermore, it is known that substitution of several nucleotides in the Shine-Dalgarno (SD) sequence, and/or in the spacer between the SD sequence and the start codon, and/or a sequence immediately upstream and/or downstream from the start codon in the ribosome-binding site (RBS) greatly affects the translation efficiency of mRNA. This modification of the RBS may be combined with decreasing transcription of at least one gene from the puuADRCBE gene cluster.

Expression of at least one gene from the puuADRCBE gene cluster can also be attenuated by insertion of a transposon or an insertion sequence (IS) into the coding region of the gene (U.S. Pat. No. 5,175,107) or in the region controlling gene expression, or by conventional methods such as mutagenesis with ultraviolet irradiation (UV) irradiation or nitrosoguanidine (N-methyl-N'-nitro-N-nitrosoguanidine). Furthermore, the incorporation of a site-specific mutation can be conducted by known chromosomal editing methods based, for example, on λRed/ET-mediated recombination.

The copy number, presence or absence of a gene from the puuADRCBE gene cluster or the entire cluster can be measured, for example, by restricting the chromosomal DNA followed by Southern blotting using a probe based on the gene sequence, fluorescence in situ hybridization (FISH), and the like. The level of gene expression can be determined by measuring the amount of mRNA transcribed from the gene using various well-known methods, including Northern blotting, quantitative RT-PCR, and the like. The amount of the protein encoded by the gene can be measured by known methods including SDS-PAGE followed by immunoblotting assay (Western blotting analysis), or mass spectrometry analysis of the protein samples, and the like.

Methods for manipulation with recombinant molecules of DNA and molecular cloning such as preparation of plasmid DNA, digestion, ligation and transformation of DNA, selection of an oligonucleotide as a primer, incorporation of mutations, and the like may be ordinary methods well-known to the person skilled in the art. These methods are described, for example, in Sambrook J., Fritsch E. F. and Maniatis T., "Molecular Cloning: A Laboratory Manual", $2^{nd}$ ed., Cold Spring Harbor Laboratory Press (1989) or Green M. R. and Sambrook J. R., "Molecular Cloning: A Laboratory Manual", $4^{th}$ ed., Cold Spring Harbor Laboratory Press (2012); Bernard R. Glick, Jack J. Pasternak and Cheryl L. Patten, "Molecular Biotechnology: principles and applications of recombinant DNA", $4^{th}$ ed., Washington, D.C., ASM Press (2009).

As explained above, the genes encoding enzymes from the transaminase pathway (patA, patD, gabT and gabD) and the glutamylated putrescine pathway (puuA, puuB, puuC, puuD, puuE and puuR) of *E. coli* have been elucidated. For the purposes of the present invention, explanations given hereinafter as to the genes from the puuADRCBE gene cluster such as puuA, puuD, puuR, puuC, puuB and puuE can be applied mutatis mutandis to the patA, patD, gabT and gabD genes.

Since there may be some differences in DNA sequences between the genera, species or strains of the family Enterobacteriaceae, the puuA, puuD, puuR, puuC, puuB and puuE genes are not limited to the genes shown in SEQ ID NOs: 1, 3, 5, 7, 9 and 11, respectively, but may include genes which are variant nucleotide sequences of or homologous to SEQ ID NOs: 1, 3, 5, 7, 9 and 11, and which encode variants of the PuuA, PuuD, PuuR, PuuC, PuuB and PuuE proteins, respectively.

The phrase "a variant protein" can mean a protein which has one or several changes in the sequence compared with SEQ ID NO: 2, 4, 6, 8, 10 or 12, whether they are substitutions, deletions, insertions, and/or additions of one or several amino acid residues, but still maintains an activity or function similar to that of the PuuA, PuuD, PuuR, PuuC, PuuB or PuuE protein, respectively, or the three-dimensional structure of the PuuA, PuuD, PuuR, PuuC, PuuB or PuuE protein is not significantly changed relative to the wild-type or non-modified protein. The number of changes in the variant protein depends on the position in the three-dimensional structure of the protein or the type of amino acid residues. It can be, but is not strictly limited to, 1 to 30, in another example 1 to 15, in another example 1 to 10, and in another example 1 to 5, in SEQ ID NO: 2, 4, 6, 8, 10 or 12. This is because some amino acids have high homology to one another so that the activity or function is not affected by such a change, or the three-dimensional structure of PuuA, PuuD, PuuR, PuuC, PuuB or PuuE protein is not significantly changed relative to the wild-type or non-modified protein. Therefore, the protein variants encoded by the puuA, puuD, puuR, puuC, puuB and puuE genes may have a homology, defined as the parameter "identity" when using the computer program BLAST, of not less than 80%, not less than 90%, not less than 95%, or not less than 98% with respect to the entire amino acid sequence shown in SEQ ID NO: 2, 4, 6, 8, 10 or 12, respectively, as long as the activity or function of the PuuA, PuuD, PuuR, PuuC, PuuB and PuuE proteins is maintained, or the three-dimensional structure of the PuuA, PuuD, PuuR, PuuC, PuuB and PuuE is not significantly changed relative to the wild-type or non-modified proteins.

The exemplary substitution, deletion, insertion, and/or addition of one or several amino acid residues can be a conservative mutation(s). The representative conservative mutation is a conservative substitution. The conservative substitution can be, but is not limited to, a substitution, wherein substitution takes place mutually among Phe, Trp and Tyr, if the substitution site is an aromatic amino acid; among Ala, Leu, Ile and Val, if the substitution site is a hydrophobic amino acid; between Glu, Asp, Gln, Asn, Ser, His and Thr, if the substitution site is a hydrophilic amino acid; between Gln and Asn, if the substitution site is a polar amino acid; among Lys, Arg and His, if the substitution site is a basic amino acid; between Asp and Glu, if the substitution site is an acidic amino acid; and between Ser and Thr, if the substitution site is an amino acid having hydroxyl group. Examples of conservative substitutions include substitution of Ser or Thr for Ala, substitution of Gln, His or Lys for Arg, substitution of Glu, Gln, Lys, His or Asp for Asn, substitution Asn, Glu or Gln for Asp, substitution of Ser or Ala for Cys, substitution Asn, Glu, Lys, His, Asp or Arg for Gln, substitution Asn, Gln, Lys or Asp for Glu, substitution of Pro for Gly, substitution Asn, Lys, Gln, Arg or Tyr for His, substitution of Leu, Met, Val or Phe for Ile, substitution of Ile, Met, Val or Phe for Leu, substitution Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

The exemplary substitution, deletion, insertion, and/or addition of one or several amino acid residues can also be a non-conservative mutation(s) provided that the mutation(s) is/are compensated by one or more secondary mutations in the different position(s) of amino acids sequence so that the activity or function of the variant protein is maintained and similar to that of the PuuA, PuuD, PuuR, PuuC, PuuB or PuuE protein, or the three-dimensional structure of PuuA, PuuD, PuuR, PuuC, PuuB or PuuE is not significantly changed relative to the wild-type or non-modified protein.

To evaluate the degree of protein or DNA homology, several calculation methods can be used, such as BLAST search, FASTA search and ClustalW method. The BLAST (Basic Local Alignment Search Tool, ncbi.nlm.nih.gov/BLAST/) search is the heuristic search algorithm employed by the programs blastp, blastn, blastx, megablast, tblastn, and tblastx; these programs ascribe significance to their findings using the statistical methods of Samuel K. and Altschul S. F. ("Methods for assessing the statistical significance of molecular sequence features by using general scoring schemes" *Proc. Natl. Acad. Sci. USA*, 1990, 87:2264-2268; "Applications and statistics for multiple high-scoring segments in molecular sequences". *Proc. Natl. Acad. Sci. USA*, 1993, 90:5873-5877). The computer program BLAST calculates three parameters: score, identity and similarity. The FASTA search method is described by Pearson W. R. ("Rapid and sensitive sequence comparison with FASTP and FASTA", *Methods Enzymol.*, 1990, 183: 63-98). The ClustalW method is described by Thompson J. D. et al. ("CLUSTAL W: improving the sensitivity of progressive multiple sequence alignment through sequence weighting, position-specific gap penalties and weight matrix choice", *Nucleic Acids Res.*, 1994, 22:4673-4680).

Moreover, the puuA, puuD, puuR, puuC, puuB and puuE genes can be variant nucleotide sequences. The phrase "a variant nucleotide sequence" can mean a nucleotide sequence which encodes the PuuA, PuuD, PuuR, PuuC, PuuB or PuuE protein using any synonymous amino acid codons according to the standard genetic code table (see, e.g., Lewin B., "Genes VIII", 2004, Pearson Education, Inc., Upper Saddle River, N.J. 07458), which can also be referred to as "a variant protein" of the PuuA, PuuD, PuuR, PuuC, PuuB or PuuE protein. The puuA, puuD, puuR, puuC, puuB and puuE genes can be variant nucleotide sequences due to degeneracy of genetic code.

The phrase "a variant nucleotide sequence" can also mean, but is not limited to a nucleotide sequence which hybridizes under stringent conditions with the nucleotide sequence complementary to the sequence shown in SEQ ID NO: 1, 3, 5, 7, 9 or 11, or a probe which can be prepared from the nucleotide sequence under stringent conditions provided that it encodes active or functional protein. "Stringent conditions" include those under which a specific hybrid, for example, a hybrid having homology, defined as the parameter "identity" when using the computer program BLAST, of not less than 70%, not less than 80%, not less than 90%, not less than 95%, not less than 96%, not less than 97%, not less than 98%, or not less than 99% is formed, and a non-specific hybrid, for example, a hybrid having homology lower than the above is not formed. For example, stringent conditions can be exemplified by washing one time or more, or in another example, two or three times, at a salt concentration of 1×SSC (standard sodium citrate or standard sodium chloride), 0.1% SDS (sodium dodecyl sulphate), or in another example, 0.1×SSC, 0.1% SDS at 60° C. or 65° C. Duration of washing depends on the type of membrane used for blotting and, as a rule, can be what is recommended by the manufacturer. For example, the recommended duration of washing for the Amersham Hybond™-N+ positively charged nylon membrane (GE Healthcare) under stringent conditions is 15 minutes. The washing step can be performed 2 to 3 times. As the probe, a part of the sequences complementary to the sequences shown in SEQ ID NO: 1, 3, 5, 7, 9 or 11 may also be used. Such a probe can be produced by PCR using oligonucleotides as primers prepared on the basis of the sequences shown in SEQ ID NO: 1, 3, 5, 7, 9 or 11 and a DNA-fragment containing the nucleotide sequence as template. The length of the probe is recommended to be >50 bp; it can be suitably selected depending on the hybridization conditions, and is usually 100 bp to 1 kbp. For example, when a DNA-fragment having a length of about 300 by is used as the probe, the washing conditions after hybridization can be exemplified by 2×SSC, 0.1% SDS at 50° C., 60° C. or 65° C.

As the genes encoding the PuuA, PuuD, PuuR, PuuC, PuuB and PuuE proteins of the species *E. coli* have already been elucidated (see above), the variant nucleotide sequences encoding variant proteins of PuuA, PuuD, PuuR, PuuC, PuuB and PuuE proteins can be obtained by PCR (polymerase chain reaction; refer to White T. J. et al., The polymerase chain reaction, *Trends Genet.*, 1989, 5:185-189) utilizing primers prepared based on the nucleotide sequences of the puuA, puuD, puuR, puuC, puuB and puuE genes; or the site-directed mutagenesis method by treating DNA containing the wild-type puuA, puuD, puuR, puuC, puuB and puuE gene in vitro, for example, with hydroxylamine, or a method for treating a microorganism, for example, a bacterium belonging to the family Enterobacteriaceae harboring the wild-type puuA, puuD, puuR, puuC, puuB and puuE genes with ultraviolet (UV) irradiation or a mutating agent such as N-methyl-N'-nitro-N-nitrosoguanidine (NTG) and nitrous acid usually used for the such treatment; or chemically synthesized as full-length gene structures. Genes encoding the PuuA, PuuD, PuuR, PuuC, PuuB and PuuE proteins or its variant proteins of other microorganisms can be obtained in a similar manner.

The phrase "a wild-type protein" can mean a native protein naturally produced by a wild-type or parent bacterial strain of the family Enterobacteriaceae, for example, by the wild-type *E. coli* MG1655 strain. A wild-type protein can be encoded by the "wild-type gene", or the "non-modified gene" naturally occurring in the genome of a wild-type bacterium.

The bacterium as described herein can be obtained by attenuating expression of at least one of the genes of the putrescine degradation pathway in a bacterium inherently having an ability to produce an L-amino acid. Alternatively, the bacterium as described herein can be obtained by imparting the ability to produce an L-amino acid to a bacterium in which expression of at least one of the genes or the putrescine degradation pathway is already attenuated.

The bacterium can have, in addition to the properties already mentioned, other specific properties such as various nutrient requirements, drug resistance, drug sensitivity, and drug dependence, without departing from the scope of the present invention.

2. Method

A method of the present invention includes the method for producing an L-amino acid such as L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine, or a mixture thereof. More specifically, a method of the present invention includes the method for producing an L-amino acid of the glutamate family such as L-arginine, L-citrulline, L-glutamic acid, L-glutamine, L-proline, and L-ornithine, or a mixture thereof. Furthermore, a method of the present invention includes the method for producing L-arginine.

The method for producing an L-amino acid can include the steps of cultivating the bacterium in a culture medium to allow the L-amino acid to be produced, excreted, and/or accumulated in the culture medium, and collecting the L-amino acid from the culture medium and/or the bacterial cells. Collected amino acid can be further purified. The L-amino acid can be produced in a salt or a hydrate form thereof, or a combination thereof. For example, sodium, potassium, ammonium, and the like salts of the L-amino acid can be produced by the method. The L-amino acid can be produced in an adduct form thereof with, for example, another organic or inorganic compound. Specifically, a monochlorhydrate salt of an L-amino acid can be produced by the method such as monochlorhydrate salt of L-lysine (L-lysine-HCl) or monochlorhydrate salt of L-arginine (L-arginine-HCl).

The cultivation of the bacterium, and collection and purification of L-amino acid, or a salt or hydrate thereof, from the medium and the like may be performed in a manner similar to conventional fermentation methods wherein L-amino acid is produced using a microorganism. The culture medium for production of the L-amino acid can be either a synthetic or natural medium such as a typical medium that contains a carbon source, a nitrogen source, a sulphur source, inorganic ions, and other organic and inorganic components as required. As the carbon source, saccharides such as glucose, lactose, galactose, fructose, sucrose, arabinose, maltose, xylose, trehalose, ribose, and hydrolyzates of starches; alcohols such as glycerol, mannitol, and sorbitol; organic acids such as gluconic acid, fumaric acid, citric acid, malic acid, and succinic acid; and the like can be used. As the nitrogen source, inorganic ammonium salts such as ammonium sulfate, ammonium chloride, and ammonium phosphate; organic nitrogen such as of soy bean hydrolyzates; ammonia gas; aqueous ammonia; and the like can be used. The sulphur source can include ammonium sulphate, magnesium sulphate, ferrous sulphate, manganese sulphate, and the like. Vitamins such as vitamin B1, required substances, for example, organic nutrients such as nucleic acids such as adenine and RNA, or yeast extract, and the like may be present in appropriate, even if trace, amounts. Other than these, small amounts of calcium phosphate, iron ions, manganese ions, and the like may be added, if necessary.

Cultivation can be performed under aerobic conditions for 16 to 72 h, or for 16 to 65 h; the culture temperature during cultivation can be controlled within 30 to 45° C., or within 30 to 37° C.; and the pH can be adjusted between 5 and 8, or between 6.5 and 7.5. The pH can be adjusted by using an inorganic or organic acidic or alkaline substance, as well as ammonia gas.

After cultivation, solids such as cells and cell debris can be removed from the liquid medium by centrifugation or membrane filtration, and then the target L-amino acid or a salt thereof can be recovered from the fermentation liquor by any combination of conventional techniques such as concentration, ion-exchange chromatography, and crystallization.

The collected target L-amino acid composition may contain microbial cells, medium components, moisture, and by-product metabolites of the microorganism in addition to the target substance. Purity of the collected target substance is 50% or higher, preferably 85% or higher, particularly preferably 95% or higher (U.S. Pat. No. 5,431,933, Japanese Patent No. 1214636, U.S. Pat. Nos. 4,956,471, 4,777,051, 4,946,654, 5,840,358, 6,238,714, U.S. Patent Published Application No. 2005/0025878).

EXAMPLES

The present invention will be more specifically explained below with reference to the following non-limiting Examples.

Example 1. Construction of *E. coli* Strain Having Inactivated the puuADRCBE Gene Cluster An *E. coli* strain having inactivated the puuADRCBE gene cluster was constructed by the method initially developed by Datsenko K. A. and Wanner B. L. called "λRed/ET-mediated integration" (Datsenko K. A. and Wanner B. L., Proc. Natl. Acad. Sci. USA, 2000, 97(12):6640-6645). A DNA-fragment containing the λattL-Cm-λattR cassette was obtained by PCR using primers P1 (SEQ ID NO: 13) and P2 (SEQ ID NO: 14) and the pMW118-λattL-Cm-λattR plasmid (WO2005010175 A1) as the template. Primer P1 contains both a region complementary to the region located at the 5'-end of the puuA gene and a region complementary to the attR region. Primer P2 contains both a region complementary to the region located at the 3'-end of the puuE gene and a region complementary to the attL region. The conditions for PCR were as follows: denaturation step for 3 min at 95° C.; profile for two first cycles: 1 min at 95° C., 30 sec at 50° C., 40 sec at 72° C.; profile for the last 25 cycles: 30 sec at 95° C., 30 sec at 54° C., 1 min 40 sec at 72° C.; final step: 5 min at 72° C.

The PCR-product obtained (about 1.6 kbp) was purified by electrophoresis in agarose gel and used for electroporation of the *E. coli* MG1655 strain containing the pKD46 plasmid having a temperature-sensitive replication origin.

The pKD46 plasmid (Datsenko K. A. and Wanner B. L., *Proc. Natl. Acad. Sci. USA*, 2000, 97(12):6640-6645) includes a 2,154 nucleotides DNA-fragment of phage λ (nucleotide positions from 31088 to 33241, GenBank accession No.: J02459), and contains genes of the λRed homologous recombination system (γ, βexo genes) under the control of the arabinose-inducible $P_{araB}$ promoter. The pKD46 plasmid is necessary for integration of a PCR-product into chromosome of the *E. coli* MG1655 strain. The *E. coli* MG1655 strain containing the recombinant plasmid pKD46 can be obtained from the *E. coli* Genetic Stock Center, Yale University, New Haven, USA (Accession No. CGSC7669).

Electrocompetent cells were prepared as follows: the *E. coli* MG1655/pKD46 strain was grown at 30° C. overnight in LB-medium (Luria-Bertani broth, also referred to as lysogenic broth; Sambrook J. and Russell D. W., Molecular Cloning: A Laboratory Manual ($3^{rd}$ ed.), Cold Spring Harbor Laboratory Press, 2001) containing ampicillin (100 mg/L); then the culture was diluted 100 times with 5 mL of SOB-medium (Sambrook J. and Russell D. W., Molecular Cloning: A Laboratory Manual ($3^{rd}$ ed.), Cold Spring Harbor Laboratory Press, 2001) containing ampicillin (100 mg/L) and L-arabinose (1 mM). The cells were grown with aeration (250 rpm) at 30° C. to $OD_{600}$ of ~0.6. Electrocompetent cells were made by concentrating 100-fold and washing three times with ice-cold deionized $H_2O$. Electroporation was performed using 70 μL of cells and about 100 ng of the PCR-product. Electroporated cells were incubated with 1 mL of SOC-medium (Sambrook J. and Russell D. W., Molecular Cloning: A Laboratory Manual ($3^{rd}$ ed.), Cold Spring Harbor Laboratory Press, 2001) at 37° C. for 2.5 hours, plated onto L-agar containing chloramphenicol (25 mg/L), and grown at 37° C. to select $Cm^R$-recombinants. To eliminate the pKD46 plasmid, two passages on L-agar supplemented with chloramphenicol (25 mg/L) at 42° C. were performed, and the obtained colonies were tested for sensitivity to ampicillin. Thus the *E. coli* MG1655ΔpuuADRCBE::Cm strain was obtained.

Example 2. Production of L-Arginine by *E. coli* 382ilvA⁺ΔpuuADRCBE

Clones of *E. coli* 382ilvA⁺ were selected as good-growing colonies on minimal agar plates. The strain 382ilvA⁺ was obtained from the L-arginine-producing strain 382 (VKPM B-7926, EP1170358 A1) by P1-transduction of the wild-type ilvA gene from *E. coli* K-12 strain. The strain 382 was deposited in the Russian National Collection of Industrial Microorganisms (VKPM) (Russian Federation, 117545 Moscow, $1^{st}$ Dorozhny proezd, 1) on Apr. 10, 2000 under the accession number VKPM B-7926 and then converted to a deposit under the Budapest Treaty on May 18, 2001. To test the effect from inactivation of the puuADRCBE gene cluster on L-arginine production, a DNA-fragment from the chromosome of the obtained *E. coli* MG1655ΔpuuADRCBE::Cm was transferred to the L-arginine-producing *E. coli* strain 382ilvA⁺ by P1-transduction (Miller, J. H. (1972) <<Experiments in Molecular Genetics>>, Cold Spring Harbor Lab. Press, Plainview, N.Y.) to obtain the *E. coli* 382ilvA⁺ΔpuuADRCBE::Cm strain.

Both *E. coli* strains 382ilvA⁺ and 382ilvA⁺ΔpuuADRCBE::Cm were each cultivated with shaking (220 rpm) at 37° C. for 18 hours in 3 mL of nutrient broth. Then 0.3 mL of the obtained cultures was inoculated into 2 mL of a fermentation medium in 20×200-mm test tubes and cultivated at 32° C. for 48 hours on a rotary shaker to an $OD_{540}$ of ~38 until glucose consumption.

After the cultivation, the amount of L-arginine which accumulated in the medium was determined by paper chromatography using a mobile phase consisting of butan-1-ol: acetic acid:water=4:1:1 (v/v). A solution of ninhydrin (2%) in acetone was used as a visualizing reagent. A spot containing L-arginine was cut out, L-arginine was eluted with a 0.5% water solution of $CdCl_2$, and the amount of L-arginine was estimated spectrophotometrically at 540 nm.

The composition of the fermentation medium (g/L) was as follows:

| | |
|---|---|
| Glucose | 48.0 |
| $(NH_4)_2SO_4$ | 35.0 |
| $KH_2PO_4$ | 2.0 |
| $MgSO_4 \cdot 7H_2O$ | 1.0 |
| Thiamine-HCl | 0.0002 |
| Yeast extract | 1.0 |
| L-Isoleucine | 0.1 |
| $CaCO_3$ | 5.0 |

Glucose and magnesium sulfate were sterilized separately. $CaCO_3$ was dry-heat sterilized at 180° C. for 2 hours. The pH was adjusted to 7.0 with KOH solution.

The results of eight independent test tube fermentations (as average values) are shown in Table 1. As it can be seen from the Table 1, the modified *E. coli* 382ilvA⁺ΔpuuADRCBE::Cm strain was able to produce a higher amount of L-arginine (Arg) as compared with the parent *E. coli* 382ilvA⁺ strain.

The *E. coli* 382ilvA⁺ΔpuuA::Km strain having inactivated the puuA gene is described in Example 5.

TABLE 1

| Production of L-arginine. | |
|---|---|
| Strain | Arg, g/L |
| *E. coli* 382ilvA⁺ (control) | 6.4 |
| *E. coli* 382ilvA⁺ΔpuuADRCBE::Cm | 7.6 |
| *E. coli* 382ilvA⁺ΔpuuA::Km | 7.5 |

Example 3. Construction of *E. coli* L-Ornithine-Producing Strain

An *E. coli* L-ornithine-producing strain was obtained from *E. coli* L-arginine-producing strain 382ilvA⁺ by inactivation of ornithine carbamoyltransferase encoded by both argF and argI genes.

3.1. Inactivation of the argF Gene

A strain in which the argF gene is deleted was constructed by the method initially developed by Datsenko K. A. and Wanner B. L. called "λRed/ET-mediated integration" (Datsenko K. A. and Wanner B. L., *Proc. Natl. Acad. Sci. USA*, 2000, 97(12):6640-6645). A DNA-fragment containing the kanamycin resistance marker ($Km^R$) was obtained by PCR using primers P3 (SEQ ID NO: 15) and P4 (SEQ ID NO: 16) and the pMW118-attL-Km-attR plasmid as the template (WO2011043485 A1). Primer P3 contains both a region complementary to the region located at the 5'-end of the argF gene and a region complementary to the attR region. Primer P4 contains both a region complementary to the region located at the 3'-end of the argF gene and a region complementary to the attL region. The conditions for PCR were as follows: denaturation step for 3 min at 95° C.; profile for two first cycles: 1 min at 95° C., 30 sec at 50° C., 40 sec at 72°

C.; profile for the last 25 cycles: 30 sec at 95° C., 30 sec at 54° C., 40 sec at 72° C.; final step: 5 min at 72° C.

The PCR-product obtained (about 1.6 kbp) was purified by electrophoresis in agarose gel and integrated into the chromosome of the *E. coli* MG1655 strain by the λRed-mediated integration as described above (Example 1) to replace the native argF gene. Thus the *E. coli* MG1655ΔargF::Km strain was obtained.

3.2. Inactivation of the argI Gene

A strain in which the argI gene is deleted was constructed by the method initially developed by Datsenko K. A. and Wanner B. L. called "λRed/ET-mediated integration" (Datsenko K. A. and Wanner B. L., *Proc. Natl. Acad. Sci. USA*, 2000, 97(12):6640-6645). A DNA-fragment containing the λattL-Cm-λattR cassette was obtained by PCR using primers P5 (SEQ ID NO: 17) and P6 (SEQ ID NO: 18) and the pMW118-attL-Cm-attR plasmid as the template (WO2005010175 A1). Primer P5 contains both a region complementary to the region located at the 5'-end of the argI gene and a region complementary to the attR region. Primer P6 contains both a region complementary to the region located at the 3'-end of the argI gene and a region complementary to the attL region. The conditions for PCR were as follows: denaturation step for 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

The PCR-product obtained (about 1.6 kbp) was purified in agarose gel and integrated into the chromosome of the *E. coli* MG1655 strain by the λRed-mediated integration as described above (Example 1) to replace the native argI gene. Thus the *E. coli* MG1655ΔargI:Cm strain was obtained.

3.3. Construction of *E. coli* Strain Having Inactivated the argI and argF Genes To obtain an *E. coli* L-ornithine-producing strain, DNA-fragments from the chromosomes of the obtained *E. coli* MG1655ΔargF::Km (Example 3.1) and *E. coli* MG1655ΔargI:Cm (Example 3.2) strains were consecutively transferred to the L-arginine-producing *E. coli* strain 382ilvA⁺ by P1-transductions to obtain the *E. coli* 382ilvA+ ΔargI:Cm ΔargF::Km strain.

The Cm$^R$ and Km$^R$-markers were eliminated simultaneously using the pMW-Int/Xis helper plasmid (WO2005010175 A1) which was electroporated into the selected plasmid-less integrants using electroporation as described above (Example 1) for electroporation of the PCR-generated DNA-fragment. After electroporation, cells were plated on L-agar containing 0.5% glucose and ampicillin (150 mg/L), and incubated at 30° C. overnight to induce synthesis of the Int/Xis proteins. The grown clones were replica-plated on L-agar with and without a mixture of chloramphenicol and kanamycin to select the Cm$^S$ and Km$^S$ (chloramphenicol and kanamycin-sensitive) variants. Thus the *E. coli* 382ilvA⁺ΔargI ΔargF strain was obtained.

Example 4. Production of L-Ornithine by *E. coli* 382ilvA⁺ΔargI ΔargF ΔpuuADRCBE::Cm To test the effect from inactivation of the puuADRCBE gene cluster on L-ornithine production, a DNA-fragment from the chromosome of the obtained *E. coli* MG1655ΔpuuADRCBE::Cm (Example 1) was transferred to the L-ornithine-producing *E. coli* strain 382ilvA⁺ΔargI ΔargF (Example 3) by P1-transduction to obtain the *E. coli* 382ilvA⁺ΔargI ΔargF ΔpuuADRCBE::Cm strain.

The L-ornithine production was evaluated as described above for L-arginine production (Example 2). The results of six independent test tube fermentations (as average values) are shown in Table 2. As it can be seen from the Table 2, the modified *E. coli* 382ilvA⁺ΔargI ΔargF ΔpuuADRCBE::Cm strain was able to produce a higher amount of L-ornithine (Orn) as compared with the parent *E. coli* 382ilvA⁺ΔargI ΔargF strain.

TABLE 2

| Production of L-ornithine. | |
| --- | --- |
| Strain | Orn, g/L |
| *E. coli* 382ilvA⁺ΔargI ΔargF (control) | 3.0 |
| *E. coli* 382ilvA⁺ΔargI ΔargF ΔpuuADRCBE::Cm | 3.7 |

Example 5. Construction of *E. coli* Strain Having Inactivated the puuA Gene

A strain in which the puuA gene is deleted was constructed by the method initially developed by Datsenko K. A. and Wanner B. L. called "λRed/ET-mediated integration" (Datsenko K. A. and Wanner B. L., Proc. Natl. Acad. Sci. USA, 2000, 97(12):6640-6645). A DNA-fragment containing the λattL-Km-λattR cassette was obtained by PCR using primers P7 (SEQ ID NO: 19) and P8 (SEQ ID NO: 20) and the pMW118-attL-Km-attR plasmid as the template (WO2011043485 A1). Primer P7 contains both a region complementary to the region located at the 5'-end of the puuA gene and a region complementary to the attR region. Primer P8 contains both a region complementary to the region located at the 3'-end of the puuA gene and a region complementary to the attL region. The conditions for PCR were as follows: denaturation step for 3 min at 95° C.; profile for two first cycles: 1 min at 95° C., 30 sec at 50° C., 40 sec at 72° C.; profile for the last 25 cycles: 30 sec at 95° C., 30 sec at 59° C., 1 min 40 sec at 72° C.; final step: 5 min at 72° C.

The PCR-product obtained (about 1.6 kbp) was purified in agarose gel and integrated into the chromosome of the *E. coli* MG1655 strain by the λRed-mediated integration as described above (Example 1) to replace the native puuA gene. Thus the *E. coli* MG1655ΔpuuA::Km strain was obtained.

Example 6. Production of L-Arginine by *E. coli* 382ilvA⁺ΔpuuA::Km

To test the effect of inactivation of the puuA gene on L-arginine production, a DNA-fragment from the chromosome of the obtained *E. coli* MG1655ΔpuuA::Km was transferred to the L-arginine-producing *E. coli* strain 382ilvA⁺ by P1-transduction to obtain the *E. coli* 382ilvA⁺ ΔpuuA::Km strain.

The L-arginine production was evaluated as described in Example 2. The results of eight independent test tube fermentations (as average values) are shown in Table 1. As it can be seen from the Table 1, the modified *E. coli* 382ilvA⁺ΔpuuA::Km strain was able to accumulate a higher amount of L-arginine as compared with the parent *E. coli* 382ilvA⁺ strain.

Example 7. Production of L-Citrulline by *E. coli* 382ΔargG ΔpuuADRCBE::Cm

To test the effect from inactivation of the puuADRCBE gene cluster on L-citrulline production, a DNA-fragment from the chromosome of the above-described *E. coli* MG1655ΔpuuADRCBE::Cm strain is transferred to the citrulline producing *E. coli* strain 382ΔargG by P1-transduction to obtain the strain 382ΔargG ΔpuuADRCBE::Cm. The strain 382ΔargG is obtained by deletion of argG gene on the chromosome of the L-arginine-producing strain 382 (VKPM B-7926, EP1170358 A1) by the method initially developed by Datsenko K. A. and Wanner B. L. called "λRed/ET-mediated integration" (Datsenko K. A. and Wanner B. L., *Proc. Natl. Acad. Sci. USA*, 2000, 97(12):6640-6645). According to this procedure, the PCR-primers homologous to both the region adjacent to the argG gene and the gene which confers antibiotic resistance in the template plasmid are constructed. The plasmid pMW118-λattL-Cm-λattR (WO2005010175 A1) is used as the template in the PCR-reaction.

*E. coli* strains 382ΔargG and 382ΔargG ΔpuuADRCBE::Cm are separately cultivated with shaking at 37° C. for 18 h in 3 mL of nutrient broth, and 0.3 mL of the obtained cultures are inoculated into 2 mL of a fermentation medium in 20×200-mm test tubes and cultivated at 32° C. for 48 h on a rotary shaker.

After the cultivation, the amount of L-citrulline which accumulates in the medium is determined by paper chromatography using a mobile phase consisting of butan-1-ol: acetic acid:water=4:1:1 (v/v). A solution of ninhydrin (2%) in acetone is used as a visualizing reagent. A spot containing citrulline is cut out, L-citrulline is eluted with 0.5% water solution of $CdCl_2$, and the amount of L-citrulline is estimated spectrophotometrically at 540 nm.

The composition of the fermentation medium (g/L) is as follows:

| | |
|---|---|
| Glucose | 48.0 |
| $(NH_4)_2SO_4$ | 35.0 |
| $KH_2PO_4$ | 2.0 |
| $MgSO_4 \cdot 7H_2O$ | 1.0 |
| Thiamine-HCl | 0.0002 |
| Yeast extract | 1.0 |
| L-Isoleucine | 0.1 |
| L-Arginine | 0.1 |
| $CaCO_3$ | 5.0 |

Glucose and magnesium sulfate are sterilized separately. $CaCO_3$ is dry-heat sterilized at 180° C. for 2 h. The pH is adjusted to 7.0.

Example 8. Production of L-Glutamic Acid by *E. coli* VL334thrC$^+$ΔpuuADRCBE::Cm To test the effect from inactivation of the puuADRCBE gene cluster on L-glutamic acid production, a DNA-fragment from the chromosome of the above-described *E. coli* MG1655ΔpuuADRCBE::Cm strain is transferred to the glutamate-producing *E. coli* strain VL334thrC$^+$ (EP1172433 A1) by P1-transduction to obtain the strain VL334thrC$^+$ ΔpuuADRCBE::Cm. The strain VL334thrC$^+$ was deposited in the Russian National Collection of Industrial Microorganisms (VKPM) (Russian Federation, 117545 Moscow, 1 Dorozhny proezd, 1) on Dec. 6, 2004 under the accession number VKPM B-8961 and then converted to a deposit under the Budapest Treaty on Dec. 8, 2004.

*E. coli* strains VL334thrC$^+$ and VL334thrC$^+$ ΔpuuADRCBE::Cm are separately cultivated for 18-24 h at 37° C. on L-agar plates. Then, one loop of the cells is transferred into test tubes containing 2 mL of fermentation medium. Cultivation is carried out at 30° C. for 3 days with shaking.

After the cultivation, the amount of L-glutamic acid which accumulates in the medium is determined by paper chromatography using a mobile phase consisting of butan-1-ol:acetic acid:water=4:1:1 (v/v) with subsequent staining by ninhydrin (1% solution in acetone), elution of the compounds in 50% ethanol with 0.5% $CdCl_2$ and further estimation of L-glutamic acid at 540 nm.

The composition of the fermentation medium (g/L) is as follows:

| | |
|---|---|
| Glucose | 60.0 |
| $(NH_4)_2SO_4$ | 25.0 |
| $KH_2PO_4$ | 2.0 |
| $MgSO_4 \cdot 7H_2O$ | 1.0 |
| Thiamine-HCl | 0.1 |
| L-Isoleucine | 0.07 |
| $CaCO_3$ | 25.0 |

Glucose and $CaCO_3$ are sterilized separately. The pH is adjusted to 7.2.

Example 9. Production of L-Proline by *E. coli* 702ilvAΔpuuADRCBE::Cm

To test the effect from inactivation of the puuADRCBE gene cluster on L-proline production, a DNA-fragment from the chromosome of the above-described *E. coli* MG1655ΔpuuADRCBE::Cm strain is transferred to the proline-producing *E. coli* strain 702ilvA by P1-transduction to obtain the strain 702ilvAΔpuuADRCBE::Cm. The strain 702ilvA was deposited in the Russian National Collection of Industrial Microorganisms (VKPM) (Russian Federation, 117545 Moscow, 1$^{st}$ Dorozhny proezd, 1) on Jul. 18, 2000 under the accession number VKPM B-8012 and then converted to a deposit under the Budapest Treaty on May 18, 2001.

*E. coli* strains 702ilvA and 702ilvAΔpuuADRCBE::Cm are separately cultivated for 18-24 h at 37° C. on L-agar plates. Then, these strains are cultivated under the same conditions as in Example 8 (Production of L-glutamic acid).

While the invention has been described in detail with reference to preferred embodiments thereof, it will be apparent to one skilled in the art that various changes can be made, and equivalents employed, without departing from the scope of the invention. All the cited references herein are incorporated by reference as a part of this application.

INDUSTRIAL APPLICABILITY

According to the present invention, production of L-amino acids such as those belonging to the glutamate family of amino acids by a bacterium of the Enterobacteriaceae family can be improved.

The invention claimed is:

1. A method for producing an L-amino acid comprising:
   (i) cultivating an L-amino acid-producing bacterium of the family Enterobacteriaceae in a culture medium; and
   (ii) collecting said L-amino acid in the culture medium, wherein said bacterium has been modified to disrupt a putrescine degradation pathway,
   wherein said bacterium belongs to the genus *Escherichia*, and
   wherein said putrescine degradation pathway is disrupted by a method selected from the group consisting of:
   (a) attenuation of expression of a gene selected from the group consisting of patA, patD, gabT, gabD, puuA, puuB, puuC, puuD, puuE, and combinations thereof, by mutating said gene, and
   (b) attenuation of expression of at least one gene from the puuADRCBE gene cluster by mutating said gene, with the proviso that the puuR gene cannot be the only gene that is attenuated; and
   wherein said L-amino acid is L-arginine or L-ornithine.

2. The method according to claim 1, wherein said putrescine degradation pathway is a transaminase pathway or a glutamylated putrescine pathway.

3. The method according to claim 1, wherein said putrescine degradation pathway is disrupted by mutating the puuA gene or the entire puuADRCBE gene cluster.

4. The method according to claim 1, wherein said gene is inactivated.

5. The method according to claim 4, wherein said gene is deleted.

6. The method according to claim 1, wherein said bacterium is *Escherichia coli*.

* * * * *